United States Patent [19]
Adler

[11] Patent Number: 5,490,416
[45] Date of Patent: Feb. 13, 1996

[54] METHOD OF DETERMINING ELASTIC AND PLASTIC MECHANICAL PROPERTIES OF CERAMIC MATERIALS USING SPHERICAL INDENTERS

[75] Inventor: Thomas A. Adler, Corvallis, Oreg.

[73] Assignee: The United States of America as represented by the Secretary of the Interior, Washington, D.C.

[21] Appl. No.: 336,120

[22] Filed: Nov. 4, 1994

[51] Int. Cl.[6] ................................................... G01N 3/42
[52] U.S. Cl. ................................................................. 73/82
[58] Field of Search ............................. 73/12.01, 81, 82, 73/818, 822

[56] References Cited

PUBLICATIONS

R. M. Anderson, T. A. Adler and J. A. Hawk, "Scale of Microstructure Effects on the Impact Resistance of A203," Wear, 162–164, Part B. 1073–1080 (1993).

Jean L. Loubet, et al "Vickers Indentation Curves of Elastoplastic Materials," Microindentation Techniques in Material Science and Engineering. ASTM STP P 889, P. J. Blau and B. R. Lawn, Eds., American Society for Testing and Materials, Philadelphia, 1986, pp. 72–89.

R. Hill, et al, "A Theoretical Studio of the Brinell Hardness Test." Proc. R. Soc. London, Ser. A, 423, 301–330 (1989).

Robert F. Cook and George M. Pharr, "Direct Observation of Indentation Cracking in Glasses and Ceramics", J. Am. Ceram. Soc., vol. 73 [4] (1990) pp. 787–817.

M. Sakai, "Energy Principle of the Indentation–Induced Inelastic surface deformation and Hardness of Brittle Materials," Acta Metall. Mater., vol. 41 No. 6 (1993) pp. 1751–1758.

J. L. Loubet, et al, "Vickers Indentation Curves of Magnesium Oxide (MgO)," Transactions of the ASME, Journal of Tribology, vol. 106 (1984) pp. 43–48.

J. S. Field, et al, "A Simple Predictive Model for Spherical Indentation," J. Mater. Res., 8 [2] 297–306 (1993).

Sheila D. Hallam, et al "Compressive brittle fracture and the construction of multi–axial failure maps" in Deformation Processes in Minerals. Ceramics and Rocks edited by D. J. Barber and P. G. Meredith, Unwin Hyman Ltd., 1990, pp. 84–108.

P. G. Meredith, "Fracture and failure of brittle polycrystals: an overviews in Deformation Processes in Minerals, Ceramics and Rocks", edited by D. J. Barber and P. G. Meredith, Unwin Hyman Ltd., 1990, pp. 5–47.

ASTM E6–89 "Standard Terminology Relating to Methods of Mechanical Testing", American Society for Testing and Materials, Philadelphia, 1989, pp. 93–102.

Lawn, et al, A model For Microcrack Initiation and Propagation Beneath Hertzian Contacts in Polycrystalline Ceramics, A. Journ. Metall. Mater. vol. 42, No. 5, pp. 1683–1693 (1994).

Marshall, David B., Geometrical Effects in Elastic/Plastic Indentation; Journal of the American Ceramic Soc., vol. 67, No. 1, pp. 57–60 (1983).

Primary Examiner—R. Raevis
Attorney, Agent, or Firm—E. Philip Koltos

[57] ABSTRACT

The invention pertains a method of determining elastic and plastic mechanical properties of ceramics, intermetallics, metals, plastics and other hard, brittle materials which fracture prior to plastically deforming when loads are applied. Elastic and plastic mechanical properties of ceramic materials are determined using spherical indenters. The method is most useful for measuring and calculating the plastic and elastic deformation of hard, brittle materials with low values of elastic modulus to hardness.

20 Claims, 20 Drawing Sheets

METHOD OF DETERMINING ELASTIC AND PLASTIC MECHANICAL PROPERTIES OF CERAMIC MATERIALS USING SPHERICAL INDENTERS

GOVERNMENT INTEREST

The invention described herein may be manufactured, used, and licensed by or for the U.S. Government for governmental purposes without the payment to me of any royalty thereon.

BACKGROUND OF THE INVENTION

1. Field of the Invention

The present invention pertains a method of determining elastic and plastic mechanical properties of ceramics, intermetallics, and other hard, brittle materials which fracture prior to plastically deforming when tensile loads are applied. The invention provides an improved means to characterize the plastic and elastic deformation of these materials. It is particularly suitable as a materials characterization method and quality control method for manufacturers and users of these materials. The method measures the plastic and elastic deformation of hard, brittle materials with low ratios of elastic modulus to hardness.

2. Description of the Prior Art

In order to comprehend the mechanisms of erosion and abrasion of ceramics, it is important to understand the load displacement relationship between an eroding or abrading particle and the material being eroded or abraded. An important part of the method to ascertain this load-displacement relationship is the determination of the stress-strain curve of the material.

In the past, the mechanical properties of hard, brittle materials have been measured by a uniaxial compression test. However, these materials fracture prior to plastically deforming in a uniaxial compression test. Uniaxial compression tests are described in P. G. Meredith, "Fracture and failure of brittle polycrystals: an overviews in Deformation Processes in Minerals, Ceramics and Rocks, edited by D. J. Barber and P. G. Meredith, Unwin Hyman Ltd., 1990, pp. 5–47; and S. D. Hallam and M. F. Ashby, "Compressive brittle fracture and the construction of multi-axial failure maps" in Deformation Processes in Minerals, Ceramics and Rocks, edited by D. J. Barber and P. G. Meredith, Unwin Hyman Ltd., 1990, pp. 84–108; among others. Mechanical properties of hard, brittle materials can also be measured by compression tests with confining hydrostatic pressure. The confining pressure can be applied through a gas, liquid or a solid medium. These apparatus are difficult to operate and are time consuming to use. When a gas or liquid is used as a confining medium, only low pressures can be applied to the test materials. Because of friction of seals and the strength of a solid medium, tests with confining pressures can be prone to considerable errors. Compression tests with confining pressures are also described in the above references. The advantages of the invention over the prior art are that the invention is easier to use and is less prone to error than the prior art. Indentation techniques are known in the art. These include J. S. Field and M. V. Swain, "A Simple Predictive Model for Spherical Indentation," J. Mater. Res., 8 [2] 297–306 (1993). However, the analyses of the contact mechanics used for these prior models do not adequately describe the load-displacement relationship between an eroding particle and the surface of the brittle material because the analyses do not adequately take into account the strain hardening of the brittle material as well as the elastic deformation. This invention characterizes such brittle materials by measuring the result of the indentation of a spherical indenter (a sphere or spherically tipped cone) and determines both plastic and elastic deformations resulting. This invention improves on other analytical indentation processes and takes into account the strain hardening of hard, brittle materials as well as the elastic deformation.

SUMMARY OF THE INVENTION

The invention provides a process for measuring the plastic and elastic deformation of a hard, brittle material having a strain to failure in a tensile test of about 0.1 or less which comprises:

(a) indenting a hard, brittle material with a rigid, solid, spherical indenter having a sphere radius of at least about 2 micrometers and a hardness of at least about 1/2.5 times the hardness of the brittle material; and (b) measuring at least one of the contact diameter plastic deformation and contact depth plastic deformation resulting from the indenting; and (c) calculating $K_2$ and $m_2$ for the spherical indenter; and (d) calculating $K_1$ and $m_1$ for the brittle material according to at least one of the equations:

$$a = \left[ \frac{C_1 u}{K_1} + \frac{C_1 u}{K_2} + \left[ \frac{u}{K_1} \right]^{\frac{1}{m_1}} + \left[ \frac{u}{K_2} \right]^{\frac{1}{m_2}} \right] D$$

$$d = \frac{C_2 u a}{K_1} + \frac{C_2 u a}{K_2} + \frac{a}{B_p} \left[ \frac{u}{K_1} \right]^{\frac{1}{m_1}} + \frac{a}{B_p} \left[ \frac{u}{K_2} \right]^{\frac{1}{m_2}}$$

wherein $$u = \frac{L}{\pi a^2}$$

$$K_1 = \frac{\pi E_1}{(1 - v_1^2)}$$

$$K_2 = \frac{\pi E_2}{(1 - v_2^2)}$$

$B_p = 1.18028 - 0.85730\, m_1 + 0.17761\, m_1^2$ $C_1 = 2.87339 + 0.19495\, m_1 + 0.63433\, m_1^2$ $C_2 = 7.02098 + 0.24729\, m_1 + 0.13521\, m_1^2$ a is the contact radius of the brittle material, $C_1$, and $C_2$ are deflection constants, $B_p$ is the profile shape ratio; $k_1$ is the elastic constant for the brittle material, $k_2$ is the elastic constant for the spherical indenter, u is the mean pressure applied; $K_1$ is the Meyer's law constant for the brittle material, $K_2$ is the Meyer's law constant for the spherical indenter, $m_1$ is the strain hardening exponent for the brittle material, $m_2$ is the strain hardening exponent for the spherical indenter, D is the diameter of the spherical indenter; d is the contact depth; L is the applied load, $E_1$ is the elastic modulus for the brittle material, $E_2$ is the elastic modulus for the spherical indenter, and $v_1$ is the Poisson's ratio for the brittle material and $v_2$ is the Poisson's ratio for the spherical indenter.

DETAILED DESCRIPTION OF THE PREFERRED EMBODIMENT

Figure 1:
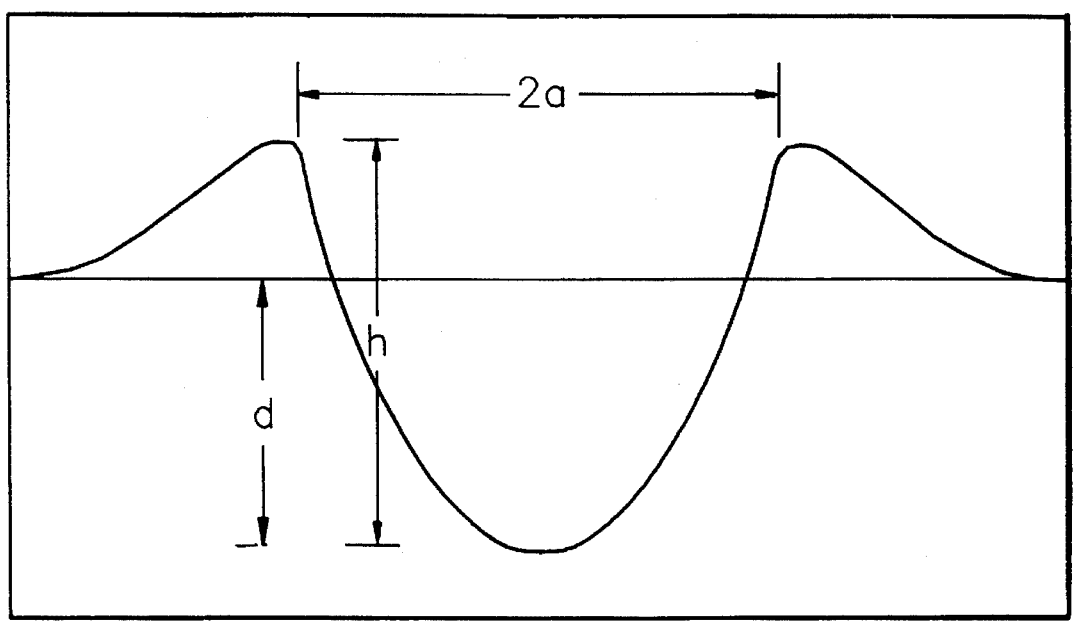
FIG. 1 shows a schematic cross section of an indentation in a rigid-plastic material that illustrates the depth d, height, h, and contact radius, a. This figure shows pile-up (h>d).

An analysis of the indentation of elastic-plastic materials is based on the analysis of the Brinell hardness test by Hill et al "A Theoretical Study of the Brinell Hardness Test." Proc. R. Soc. London, Ser. A, 423, 301–330 (1989), which is incorporated herein by reference. This analysis includes relationships among contact pressure, plastic strain, strain hardening, the depth of penetration and the amount of "pile-up" and "sinking-in". For the Brinell hardness test the surface of the material to be tested is indented with a hardened steel or tungsten carbide ball. The hardness is the load divided by the contact area. The projected area is the preferred divisor for calculating hardness, since this value of hardness can be directly related to the flow stress. The geometry of the indentation is shown in FIG. 1. Depth, d, is the displacement of the surface from the original position to the bottom of the contact area. Height, h, is the displacement from the edge of the contact area to the bottom of the contact area. The radius of the contact area is a.

In a study of indentation of metals by spheres, Meyer found that the hardness, H, followed a simple power law. See E. Meyer, "Untersuchugen über Prufung and Härte", Zeit. Ver Deutche Ing., 52, 645–654 (1908):

$$H = \frac{L}{\pi a^2} = K \left[ \frac{a}{D} \right]^m \quad (1)$$

where L is the maximum force on the indenter, K and m are material constants, and D is the diameter of the ball. This dependence has been verified numerous times for metals. O'Neill showed that the strain hardening exponent, m, in Meyer's law is related to the true stress-strain curve in uniaxial tension, when the material follows a power hardening law. See H. O'Neill, "Significance of Tensile and Other Mechanical Tests of the Properties of Metals," Proc. Inst. Mech. Engr., 151, 116–130 (1944):

$$\sigma = g\epsilon^m \quad (2)$$

where $\sigma$ is stress, $\epsilon$ is strain, and g and m are material constants. The exponent, m, is the same for both the tensile stress-strain curve and Meyer's law. Meyer's law is valid for any material, as long as the tensile stress-strain curve can be approximated by equation 2.

Tabor demonstrated that there is a representative strain that could be associated with spherical indentations. See D. Tabor, The Hardness of Metals, Oxford University Press, London, 1951. This representative strain, $\epsilon$, is independent of the strain hardening exponent and is a function of the ratio a/D or a/R.

$$\epsilon = 0.4 \frac{a}{D} = 0.2 \frac{a}{R} \quad (3)$$

where R is the radius of the ball. The average contact pressure is 2.8 times the flow stress in a tensile test for a strain equal to the representative strain.

$$\frac{L}{\pi a^2} = 2.8\sigma \quad (4)$$

Equation 5 follows after substitution of equations 2 and 3 for a and $\epsilon$.

$$\frac{L}{\pi a^2} = 2.8g \left[ 0.4 \frac{a}{D} \right]^m \quad (5)$$

By combining equations 1 and 5, there is a relation between K and g.

$$K = \alpha \beta^m g \quad (6)$$

The value of $\alpha$ is 2.8 and $\beta$ is 0.4. The empirical relationships of equations 3 to 6 are valid for any material that follows a power hardening law (equation 2). The ratio of the height, h, to the depth, d, is a constant that depends only on the strain hardening exponent, m, and is independent of load, L. This ratio is defined as B:

$$B = \frac{h}{d} \quad (7)$$

This is valid for materials that followed the power hardening law, equation 2. The value of B is a slowly varying function of m as listed in Table I.

The contact pressure between a sphere and a flat surface has the following the equation:

$$p(r) = \left[ 1 + \frac{s}{2} \right] \left[ 1 - \frac{r^2}{a^2} \right]^{\frac{s}{2}} \frac{L}{\pi a^2} \quad (8)$$

where r is the distance from the center of the contact area and s is a constant that depends on the strain hardening exponent, m. However, the constant, s, is equal to m only for the special case of m=1. Other values of s are listed in Table I. The contact pressure is not uniform for a rigid plastic material, but is a maximum at r=0 and is zero at r=a. The amount of "pile-up" and "sinking-in" (parameter B) can also be directly related to the strain hardening exponent, m, and the pressure distribution exponent, s:

$$B = \left[ \frac{2-m}{4+m} \right] \left[ 2 + \frac{s}{2} \right] \quad (9)$$

Equation 9 completes the consistent picture of the relationships between the profile shape, B, the contact pressure, p, the representative strain, $\epsilon$ and the strain hardening exponent, m, for the indentation of plastic materials by spherical indenters. There is a load below which the plastic analysis can not be used. For lighter loads, the contact between a sphere and a flat will be totally elastic, and the above analysis will not be valid. The plastic analysis should only be used for loads that cause the indentation to be "fully plastic". However, the fully plastic limit is not well defined. Meyer suggested a lower limit of a/D= 0.05. Tabor presented data that indicates a lower limit of a/D=0.1 for hardened steel. Hill suggested a lower limit for the fully plastic regime of a/D=0.01. The results of the plastic analysis should only apply to indentations with ratios of a/D greater than this lower limit.

The analysis by Hill modelled plastic materials as non-linear elastic solids. This analysis is valid as long as unloading does not occur, which is applicable for indentation of plastic materials by spheres. In order to relate the analysis of Hill to the yield stress, the non-linear analysis can be related to incremental plastic deformation. For the incremental plasticity, a rigid-plastic material can be assumed and the Levy-Mises equations can be used. The yield stress can be defined as the stress for 0.002 plastic strain. In this case, the yield stress, Y, is related to the power law constant g with equation 2.

$$Y = g \, (0.002)^m \quad (10)$$

The Meyer's law constant can then be related to the yield stress by combining equations 6 and 10.

$$Y = \frac{K \, (0.005)^m}{2.8} \quad (11)$$

For materials with large hardness to elastic modulus ratios, the elastic deformation must be considered in the indentation analysis. Analysis of the stresses and strains should follow the Reuss equations instead of the Livy-Mises equations. For elastic-plastic materials the indentation will be analyzed by adding the displacements from a rigid-plastic material to the displacements for an elastic contact. The pressure distribution is the same for the elastic and plastic components, and are equal to the pressure distribution for the more compliant of the two components, which is the plastic component as in equation 8. The displacements at the bottom of the indentation and the displacements at the edge of the indentation are the sum of the elastic and plastic components.

$$d = d_e + d_p \quad (12)$$

$$h = h_e + h_p \quad (13)$$

Figure 2A:
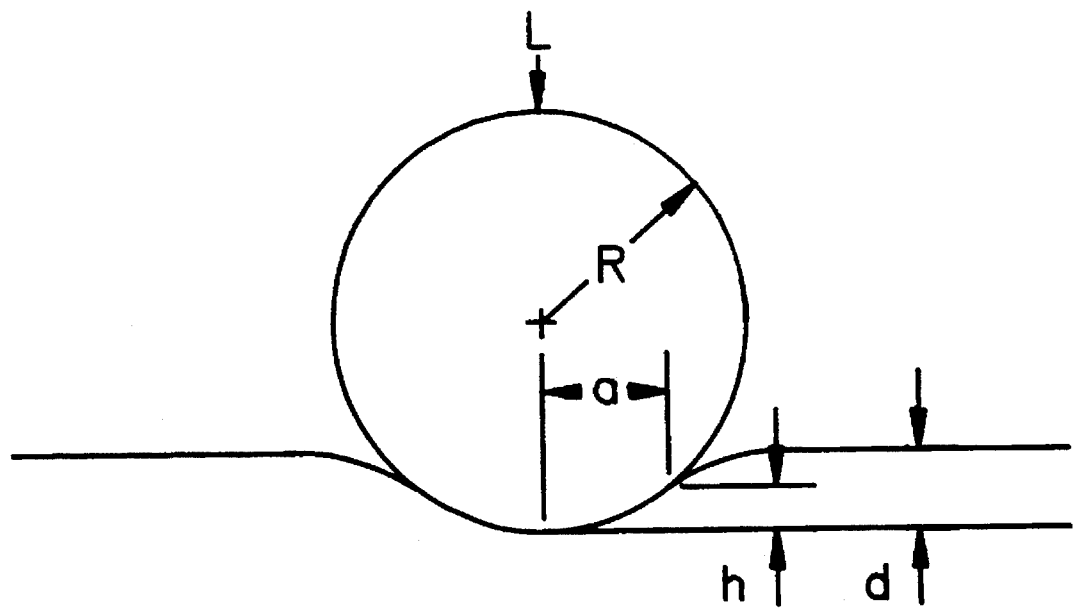
FIGS. 2a and 2b show schematic cross sections of an indentation in an elastic-plastic material a) loaded and b) unloaded. The contact radius, a, heights, h and $h_p$, and depths, d and $d_p$ are shown. This schematic shows sinking-in (hp<dp).
Figure 2B:
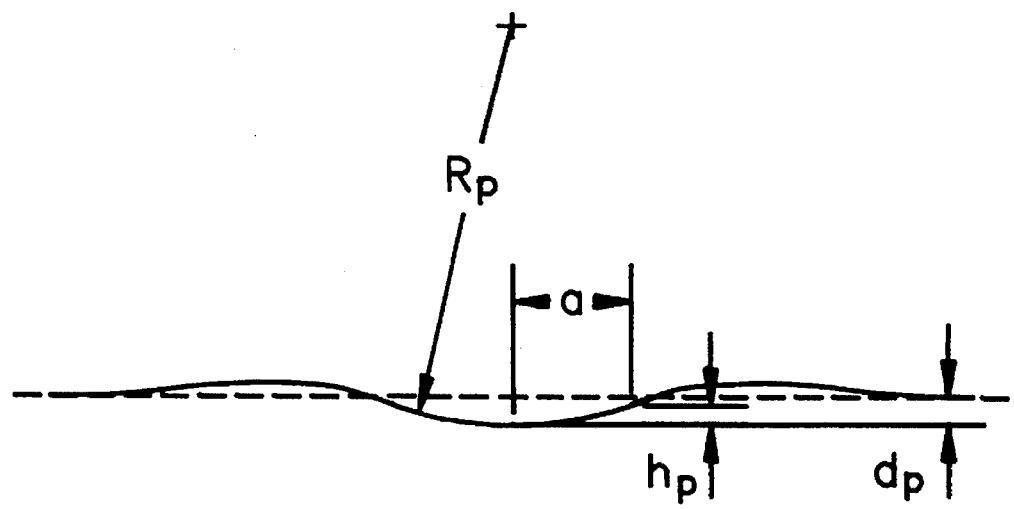

The height, h, and depth, d with the load applied are illustrated in FIG. 2a, while the residual, unloaded height, $h_p$, and depth, $d_p$, are illustrated in FIG. 2b.

The representative strain, $\epsilon$, can also be separated into plastic and elastic components. This can be done by using the geometric relation between a, D, and h.

$$\frac{a}{D} = \frac{h}{a} \quad (14)$$

Then, substitute h/a for a/D in equation 3:

$$\epsilon = .04 \left[ \frac{h}{a} \right] = 0.4 \left[ \frac{h_e}{a} + \frac{h_p}{a} \right] \quad (15)$$

The plastic representative strain, $\epsilon_p$, is the strain that would be produced by a sphere with a larger diameter $D_p$, indenting a rigid plastic material with the same plastic deformation properties i.e., the same K and m:

$$\epsilon_p = 0.4 \frac{h_p}{a} = .04 \frac{a}{d_p} \quad (16)$$

The elastic representative strain, $\epsilon_e$ is the strain that would be produced by a larger diameter sphere, $D_e$, indenting a material with the same elastic properties and no plastic deformation assuming the pressure distribution in equation 8.

$$\epsilon_e = 0.4 \frac{h_e}{a} = 0.4 \frac{a}{D_e} \quad (17)$$

The end result is that the indentation of a elastic plastic material is equivalent to indentation of a rigid plastic material wide a larger radius sphere, $R_p$, as shown in FIG. 2. The elastic and plastic diameters or radii are related to each other by equation 18.

$$\frac{1}{D_p} = \frac{1}{D} - \frac{1}{D_e} \quad \frac{1}{R_p} = \frac{1}{R} - \frac{1}{R_e} \quad (18)$$

When the elastic component of strain is removed, modified forms of Meyer's law result, equation 19 or 20.

$$H = \frac{L}{\pi a^2} = K \left[ \frac{a}{D_p} \right]^m \quad (19)$$

$$H = \frac{L}{\pi a^2} = K \left[ \frac{h_p}{a} \right]^m \quad (20)$$

The stresses and strains for elastic plastic indentation can be related to the tensile stress-strain properties when the tensile stress strain relationship can be approximated by equation 21.

$$\epsilon = \epsilon_e + \epsilon_p = \frac{\sigma}{E} = \left[ \frac{\sigma}{g} \right]^{\frac{1}{m}} \quad (21)$$

$$\sigma = g \, (\epsilon_p)^m \quad (22)$$

As with rigid plastic indentation, the average contact pressure will be 2.8 times the flow stress, except that the flow stress is dependent only on the plastic strain. Equation 23 follows from substitution of equations 22 and 16 for $\sigma$ and $\epsilon$ in equation 4.

$$\frac{L}{\pi a^2} + 2.8g \left[ 0.4 \frac{a}{D_p} \right]^m \quad (23)$$

By combining equations 19 and 23, the relationships between the Meyer's law constant, K, the power law constant, g, and the yield stress, Y, remain the same as for the rigid plastic material, equations 6, 10 and 11. During the loading cycle of the indentation, the profile of the indentation is effected by both elastic and plastic deformation, equations 12 and 13. After unloading, only the plastic residual components of the displacements remain, $d_p$ and $h_p$, as shown in FIG. 2. The ratio of the residual height, $h_p$, to the residual depth, $d_p$, is designated $B_p$.

$$B_p = \frac{h_p}{d_p} \quad (24)$$

The ratio for the residual profile, $B_p$, should depend only on the strain hardening exponent, m, in the same manner as Hill found for rigid plastic material, as listed in Table I. The relation between the profile shape ratio, $B_p$, strain hardening exponent, m, and pressure distribution exponent, s, should also apply to elastic plastic indentation. This is given by equation 9, after substituting $B_p$ for B.

Figure 3:
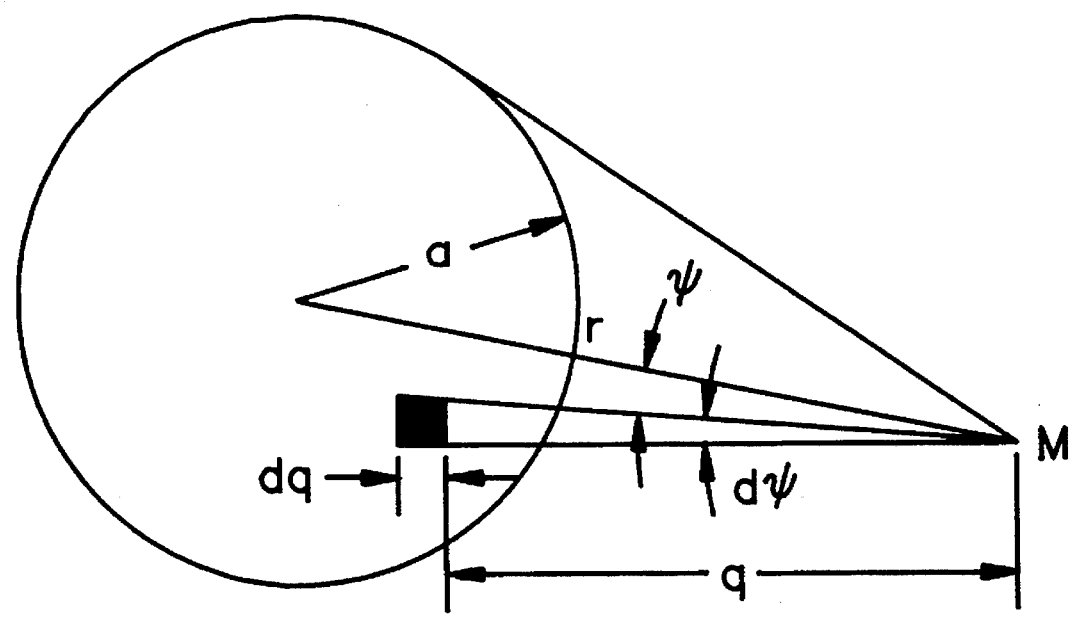
FIG. 3 shows a schematic representing the parameters used in calculating the elastic deflection.

The elastic displacements, $d_e$ and $h_e$, are calculated from the pressure distribution, equation 8. The geometry of the contact is shown in FIG. 3. An element of the contact area is $qdqd\psi$, the distance from the point M to the element of the loaded area is q, and Poisson's ratio is v. The general formula for the elastic displacements, w, at a point M is equation 25.

$$w = \frac{(1-v^2)}{\pi E} \iint p \, dq \, d\psi \quad (25)$$

Figure 4:
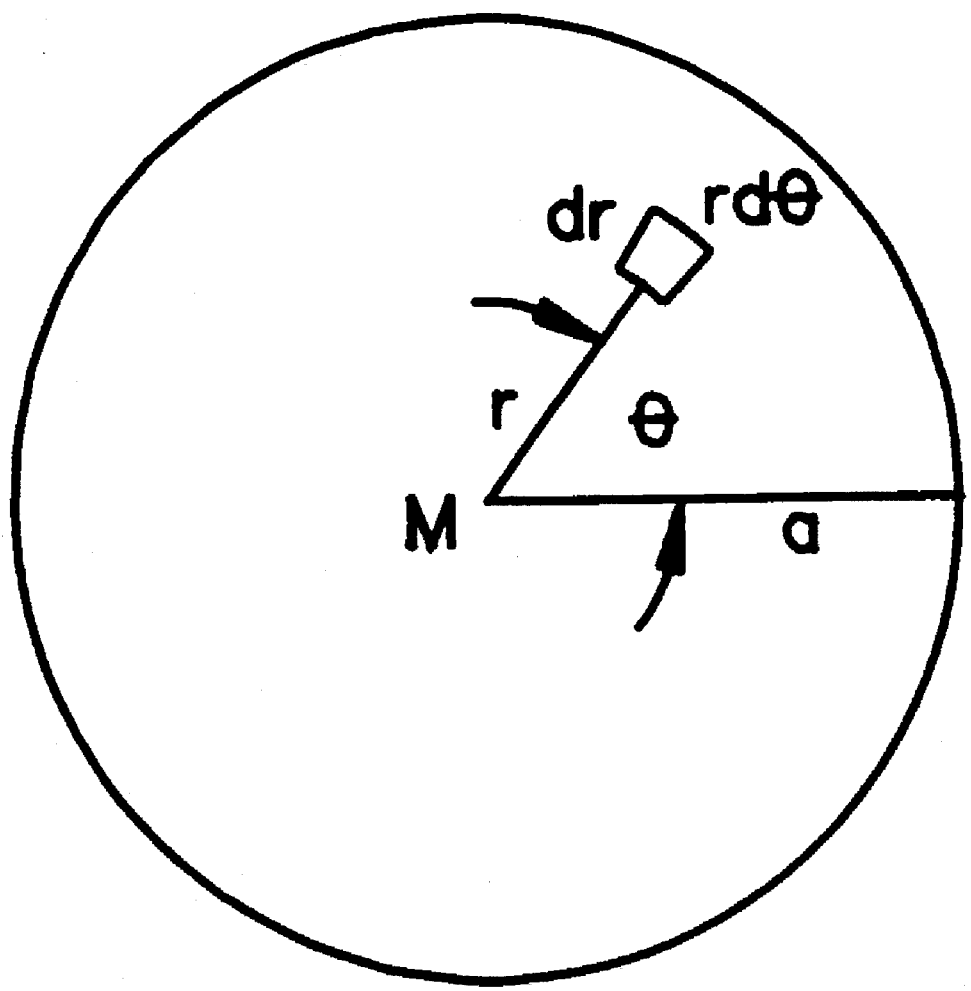
FIG. 4 is a schematic showing the parameters used in calculating the elastic deflection of a point at the center of the contact area.

When the point M is at the center of the contact area, as shown in FIG. 4, the displacement is the depth, $d_e$.

$$d_e = w = \frac{1}{K} \int_0^{2\pi} \int_0^a p \, dr \, d\theta \quad (26)$$

The constant, k, is given in equation 27.

$$K = \frac{\pi E}{(1-v^2)} \quad (27)$$

Equation 8 is substituted for p in equation 26.

$$d_e = \frac{1}{K} \int_0^{2\pi} \int_0^a \left[ 1 + \frac{s}{2} \right] \left[ 1 - \frac{r^2}{a^2} \right]^{\frac{s}{2}} u \, dr \, d\theta \quad (28)$$

The mean pressure, u, is given by equation 29.

$$u = \frac{L}{\pi a^2} \quad (29)$$

The integral in equation 28 is solved for a material with strain hardening exponent m=1/10, and s=0.64.

$$d_e = \frac{7.055ua}{K} \quad (30)$$

Figure 5:
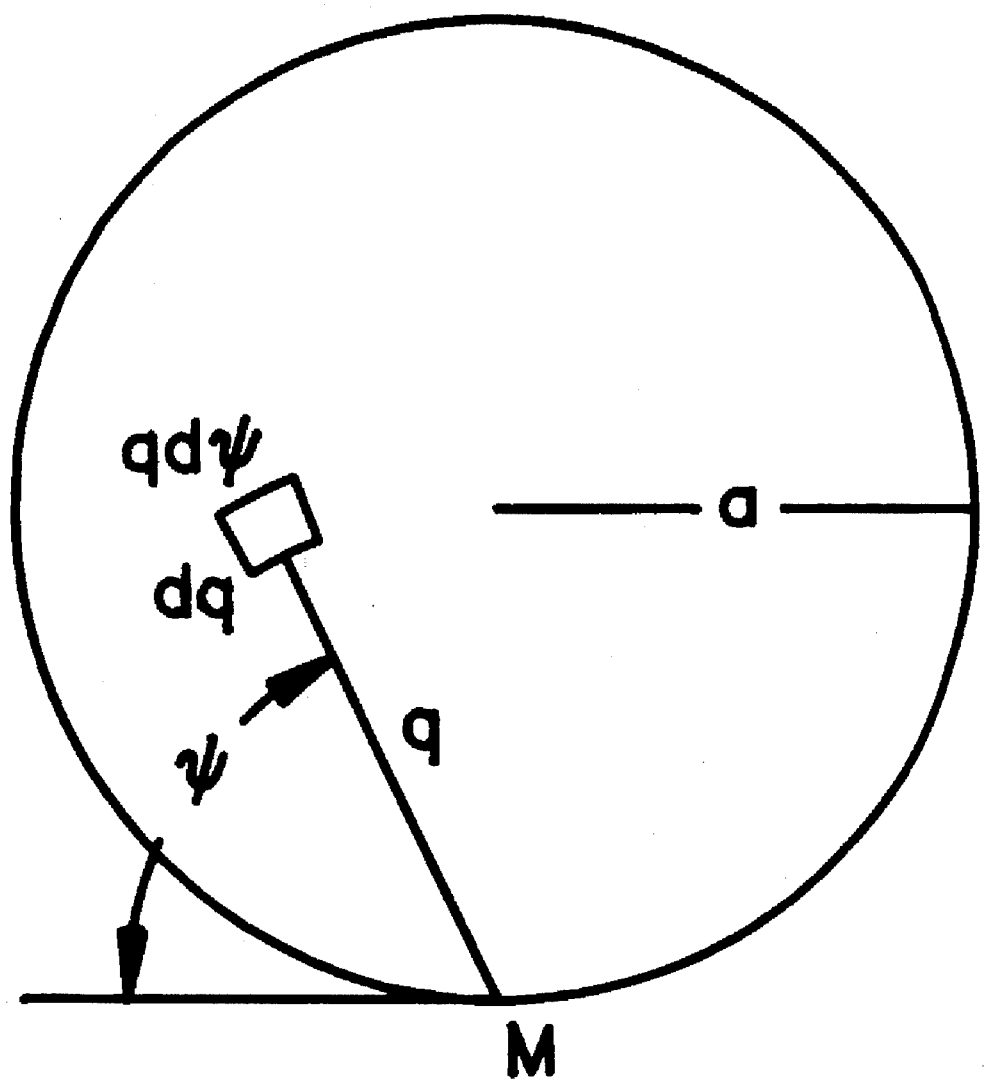
FIG. 5 is a schematic showing the parameters used in calculating the elastic deflection of a point on the edge of the contact area.

When the point M is at the edge of the area of contact as shown in FIG. 5, the displacement is equal to the difference between the depth, $d_e$, and the height, $h_e$.

$$w = d_e - h_e = \frac{2}{K} \int_0^{\frac{\pi}{2}} \int_0^{2a\sin\psi} p \, dq \, d\psi \quad (31)$$

After substitution for p the integral in equation 31 was solved for m=1/10 and s=0.64.

$$w = \frac{4.146ua}{K} \quad (32)$$

The height, $h_e$, is found by subtracting the displacement, w, from the depth, $d_e$.

$$h_e = \frac{2.909ua}{K} \quad (33)$$

The case for m=1 and s=1 is the elastic contact is solved by $$d_e = \frac{3\pi^2 ua}{4K} = \frac{7.4022ua}{K} \quad (34)$$

$$h_e = \frac{3\pi^2 ua}{8K} = \frac{3.7011ua}{K} \quad (35)$$

Another pressure distribution, often used for elastic-plastic indentations is uniform pressure when s=0.

$$d_e = \frac{2\pi ua}{K} = \frac{6.283ua}{K} \quad (36)$$

$$h_e = \frac{(2\pi - 4)ua}{K} = \frac{2.283ua}{K} \quad (37)$$

Uniform pressure contacts do not occur for rigid plastic materials that follow a power law hardening, equation 2. The extension to elastic-plastic materials indicates that a uniform pressure distribution does not occur for materials that follow equation 21. The numerical constant in equations 30, 33, 34, 35, 36, and 37 can be replaced by constants $C_1$ and $C_2$.

$$h_e = \frac{C_1 ua}{K} \quad (38)$$

$$d_e = \frac{C_2 ua}{K} \quad (39)$$

The values of constants $C_1$ and $C_2$ are listed Table I.

The elastic height, $h_e$ in equation 38, can be subtracted from the total height, h, to give the residual plastic height, $h_p$.

$$h_p = h - h_e = \frac{a^2}{D} - h_e \quad (40)$$

Equation 40 is substituted for $h_p$ in equation 20.

$$\frac{L}{\pi a^2} = K \left[ \frac{a}{D} - \frac{h_e}{a} \right]^m \quad (41)$$

Equation 29 is used for the mean pressure, u, and equation 38 is used for the height, $h_e$ $$u = K \left[ \frac{a}{D} - \frac{C_1 u}{K} \right]^m \quad (42)$$

Equation 42 is used to find the Meyer's law constants, K and m from the load, L, and radius, a, data assuming the elastic modulus is known from another method and assuming the indenter is rigid. Once K and m are determined, the radius, a, depth, d, height, h, and load, L, can be calculated as a function of the mean pressure.

$$a = \left[ \frac{C_1 u}{K} + \left[ \frac{u}{K} \right]^{\frac{1}{m}} \right] D \quad (43)$$

$$d = \frac{C_2 ua}{K} + \frac{a}{B_p} \left[ \frac{u}{K} \right]^{\frac{1}{m}} \quad (44)$$

$$h = \frac{C_1 ua}{K} + a \left[ \frac{u}{K} \right]^{\frac{1}{m}} \quad (45)$$

-continued $$L = \pi a^2 u \quad (46)$$

The preceding analysis is based on the assumption that the sphere or indenter is a rigid solid. Deformation of the sphere can be analyzed in the same manner as the flat specimen. The displacements and properties of the sphere will be designated with a subscript 2 and the flat specimen will be designated with a subscript 1. The total height, h, will have four components.

$$h = h_{p1} + h_{p2} + h_{e1} + h_{e2} \quad (47)$$

The formula for the mean pressure, u is equation 48.

$$u = K_1 \left[ \frac{a}{D} - \frac{C_1 u}{K_1} - \frac{C_1 u}{K_2} - \left[ \frac{u}{K_2} \right]^{\frac{1}{m_2}} \right]^{m_1} \quad (48)$$

Then the formula for the contact radius is equation 49.

$$a = \left[ \frac{C_1 u}{K_1} + \frac{C_1 u}{K_2} + \left[ \frac{u}{K_1} \right]^{\frac{1}{m_1}} + \left[ \frac{u}{K_2} \right]^{\frac{1}{m_2}} \right] D \quad (49)$$

Similarly, equations for the diameter of an equivalent sphere, $D_p$, the depth, d, and the height, h, can be written by changing equations 18, 44, and 45 from two terms to four terms.

$$d = \frac{C_2 u a}{K_1} + \frac{C_2 u a}{K_2} + \quad (49a)$$

$$\frac{a}{B_p} \left[ \frac{u}{K_1} \right]^{\frac{1}{m_1}} + \frac{a}{B_p} \left[ \frac{u}{K_2} \right]^{\frac{1}{m_2}}$$

In these equations, a is the contact radius on the brittle material, $C_1$, $C_2$ and $B_p$ are constants that are a function of the strain hardening exponent; $k_1$ and $k_2$ are constants that depend on the elastic properties of the material, u is the mean pressure; $K_1$ and $K_2$ are the Meyer's law constants, $m_1$ and $m_2$ are the strain hardening exponents, D is the diameter of the indenter; and d is the contact depth.

One component of elastic deformation was not taken into account in the analysis. This component results in residual elastic stresses around the indentation after unloading and is not present in the analysis of Hill. The residual elastic stresses results from the irreversible plastic deformation causing compressive stresses parallel to the surface. The residual elastic compressive stress is small compared to the mean pressure, u, and therefore causes only a secondary effect. To keep the analysis relatively simple, residual elastic stresses were ignored. However, these stresses would have to be considered in a more rigorous treatment of elastic-plastic deformation.

The method has very broad ranges of conditions. The temperature range is limited only by the highest temperature at which a sphere or spherical indenter can be pressed into a sample. The sphere radius can be as small as 2 micrometers. The sphere size is limited on the high end only by the size of a load frame to make the indentation. It is possible to indent materials with indenter radius as low as 2 micrometers with loads as low as 25 micronewtons. The spheres can be made out of any material that will withstand the loads without excessive deformation or fracture. At a minimum, the sphere should be greater than 1/2.5 of the hardness of the sample, but best results will be for spheres or spherical indenters harder than the sample.

Other devices may be used to measure the depth of the indentation, while the load is being applied, instead of measuring the diameter of the indentation after the load is removed. The analysis would be based on equation 49a, instead of equation 48. Such alternative measurement techniques are described in the following references, although not previously applied to indentation of brittle materials with spherical indenters with the results estimating the stress-strain curve. J. S. Field and M. V. Swain, "A Simple Predictive Model for Spherical Indentation," J. Mater. Res., 8 [2] 297–306 (1993), Jean L. Loubet, Jean M. Georges, and Gerard Meille, "Vickers Indentation Curves of Elastoplastic Materials," Microindentation Techniques in Material Science and Engineering. ASTM STP P 889, P.J. Blau and B. R. Lawn, Eds., American Society for Testing and Materials, Philadelphia, 1986, pp. 72–89; J. L. Loubet, J. M. Georges, O. Marchesini and G. Meille, "Vickers Indentation Curves of Magnesium Oxide (MgO)," Transactions of the ASME, Journal of Tribology, Vol. 106 (1984) pp. 43–48, Robert F. Cook and George M. Pharr, "Direct Observation of Indentation Cracking in Glasses and Ceramics", J. Am. Ceram. Soc., Vol. 73 [4] (1990) pp. 787–817; M. Sakai, "Energy Principle of the Indentation-Induced Inelastic surface deformation and Hardness of Brittle Materials," Acta Metall. Mater., Vol 41 No. 6 (1993) pp. 1751–1758. All of these are incorporated herein by reference.

This invention is suitable for use when the hardness of the indenter $H_i$ and the hardness of the material $H_m$ have the relationship $H_i/H_m > 0.4$, preferably $>1.0$ and most preferably $>2.5$. For lower indenter hardness, the brittle material does not plastically deform. For materials with a strain to failure in a tensile test greater than 0.10, the material is ductile. For materials with a strain to failure in a tensile test of less than 0.10, the material is brittle. In the process of the invention, the indenter indents the brittle material with a force of at least 25 micronewtons and preferably from about 9.8 millinewtons to about 29,400 newtons. In the preferred embodiment, the spherical indenter has a sphere radius ranging from about 2 micrometers to about 5 millimeters and a cone angle ranging from about 90° to about 150°. Also in the preferred embodiment, The spherical indenter has a hardness greater than about 2.5 times the hardness of the brittle material and the brittle material has a strain to failure ratio of less than about 0.01. In addition, it is preferred that the brittle material is polished prior to indenting, such as to a finish of less than about 1 micrometer. In the most preferred embodiment, the brittle material is a ceramic material, however, it can also comprise a metal, intermetallic or rock.

The following non-limiting example serves to illustrate the invention.

EXAMPLE 1

Three series of indentation tests follow. Alumina was indented with diamond, tungsten carbide-cobalt was indented with diamond, and alumina was indented with tungsten carbide-cobalt spheres. The 99.5% alumina (Coors Ceramic Company, Golden, Colo.) was in the form of 30 mm thick plate. The alumina specimens were either cubes or cylinders with all dimensions greater than 10 mm. Prior to indentation, all specimens were polished through a series of diamond grades ultimately to a ¼ micrometer finish. Grain size measurements were performed on polished and thermally etched (i.e., 1550° C. for 20 minutes) alumina disks. Grain sizes of each sample were determined with an image analysis system (Kontron Electronic GmbH, Eching Germany). The Archimedes method utilizing water as the immersion medium was used to determine the densities of the ceramic samples. The Vickers hardness, determined with a one kilogram load, was 13.2 GPa (1344 kg/mm²).

The WC-Co spheres were 1.69 mm in diameter and had a Vicker's hardness of 15.1 GPa (1535 kg/mm$^2$). In order to determine the Meyer's law constants for the WC-Co some of the spheres were sectioned and polished for indentation by the diamond indenters. The diamond indenters were in the shape of spherical tipped cones. The radius of the tips were 2.023, 0.963, 0.553, and 0.216 mm. The smallest radius indenter was a Rockwell A indenter, with a 120° cone angle. The diamonds with the 2.023 and 0.963 mm radius tip had 120° cone angles and the diamond with the 0.553 mm tip radius had a 90° cone angle.

Some of the indentations were made by mounting the 1.69 mm WC-Co ball to a Rockwell hardness tester. Three to five measurements at loads of 60, 100, and 150 kg were made in alumina specimens. Additional indentations at loads not obtainable with a Rockwell tester (at 200 and 250 kgf loads) were made by mounting the alumina sample on a screw driven universal testing machine (Instron, Canton, Mass.) and then pushing a WC-Co ball into the sample. A crosshead speed of 0.5 mm/min was used in each test with the universal tester. The Rockwell A scale indenter was used with the Rockwell tester to indent the alumina at loads of 15, 30, and 60 kgf and the WC-Co at 15 and 30 kgf. The other spherically tipped diamonds were used to indent the WC-Co and alumina with the universal testing machine. The Rockwell A diamond was also used to make indentations with the universal tester to check for differences between the Rockwell tester and the universal testing machine. No differences were observed. The depth and diameter of the indentations were measured by tracing profiles through the center of the indentations with a surface analyzer, digitally storing the profiles, and then calculating the depth and diameter from stored profiles. This method was reproducible to about 3 micrometers diameter and 0.05 micrometers in depth.

Figure 6:
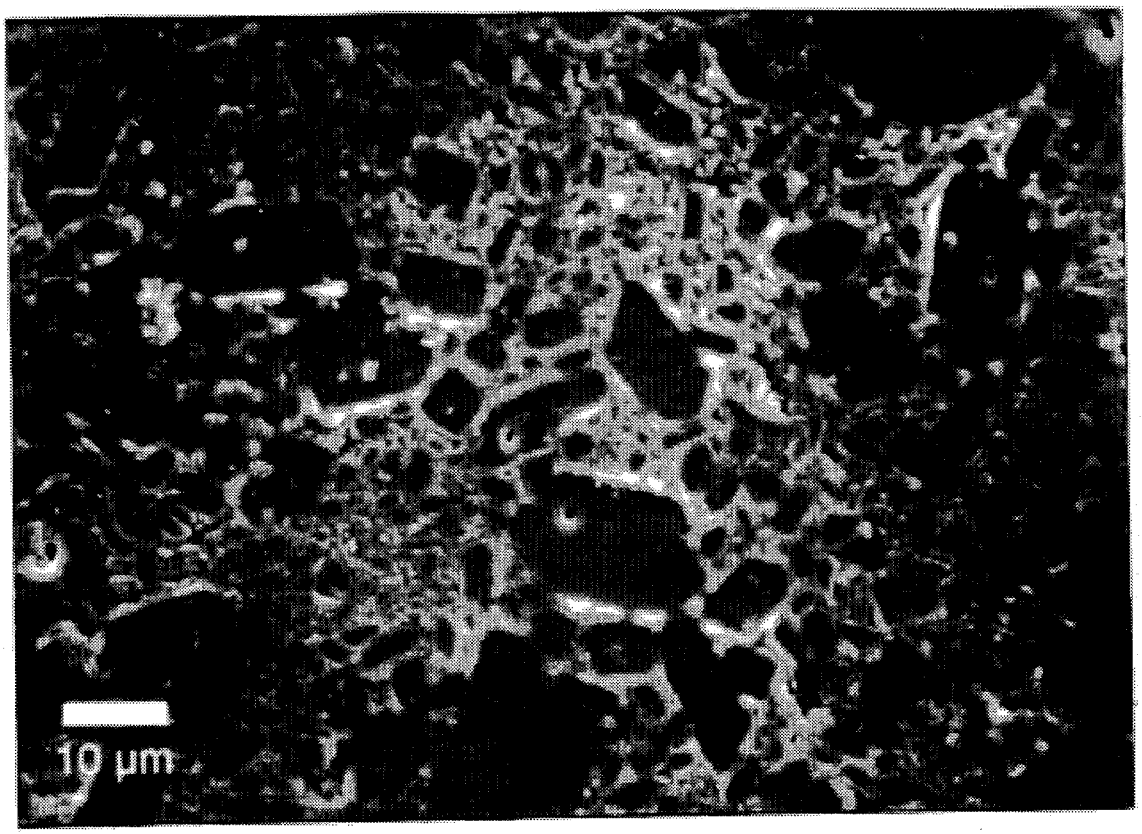
FIG. 6 shows a scanning electron micrograph of typical microstructure for thermally etched alumina.

Representative microstructure of the alumina is shown in FIG. 6. The grain size of the alumina is bimodal in nature with a large fraction of grains finer than 1 micrometer and a second mode at 8 micrometers. The overall mean grain size for alumina is 3 micrometers. The alumina exhibited zero water absorption and a density of 3900 kg/m$^3$ which indicates that the volume of porosity is less than 2 percent.

Figure 7:
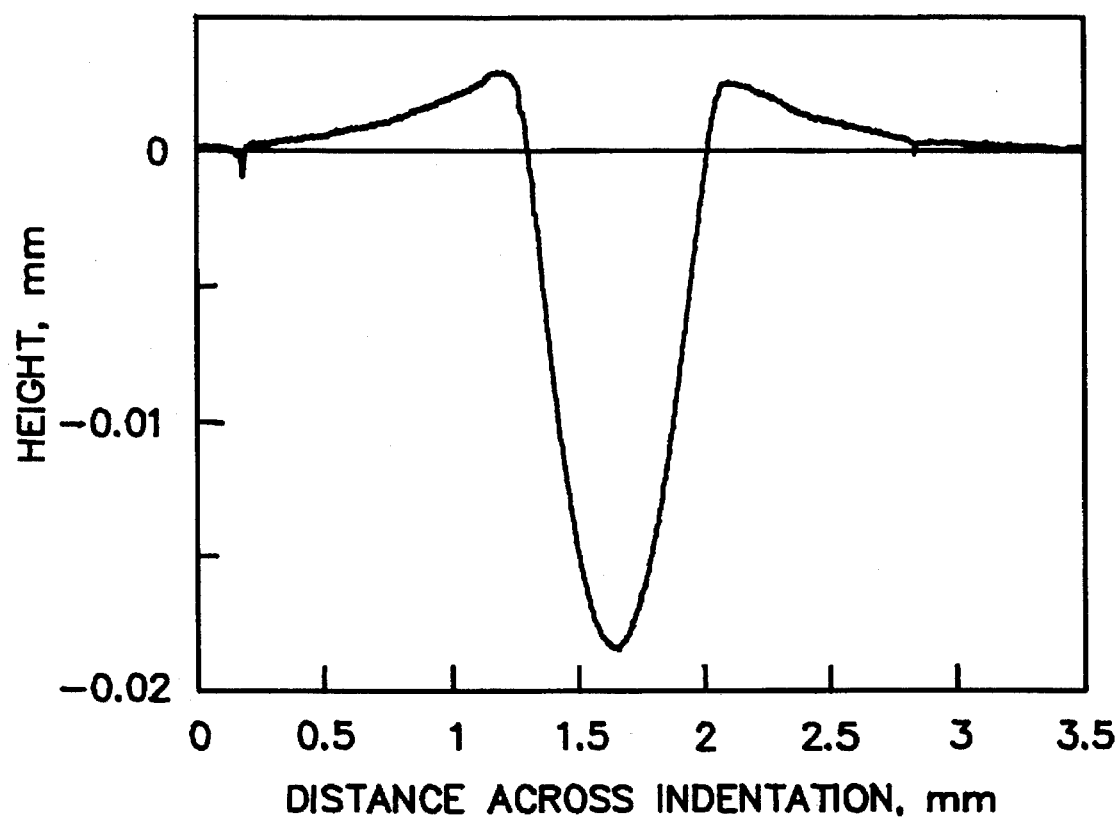
FIG. 7 shows a profile of indentation in alumina made by 2.02 mm radius diamond with 6420N (655 kgf).
Figure 8:
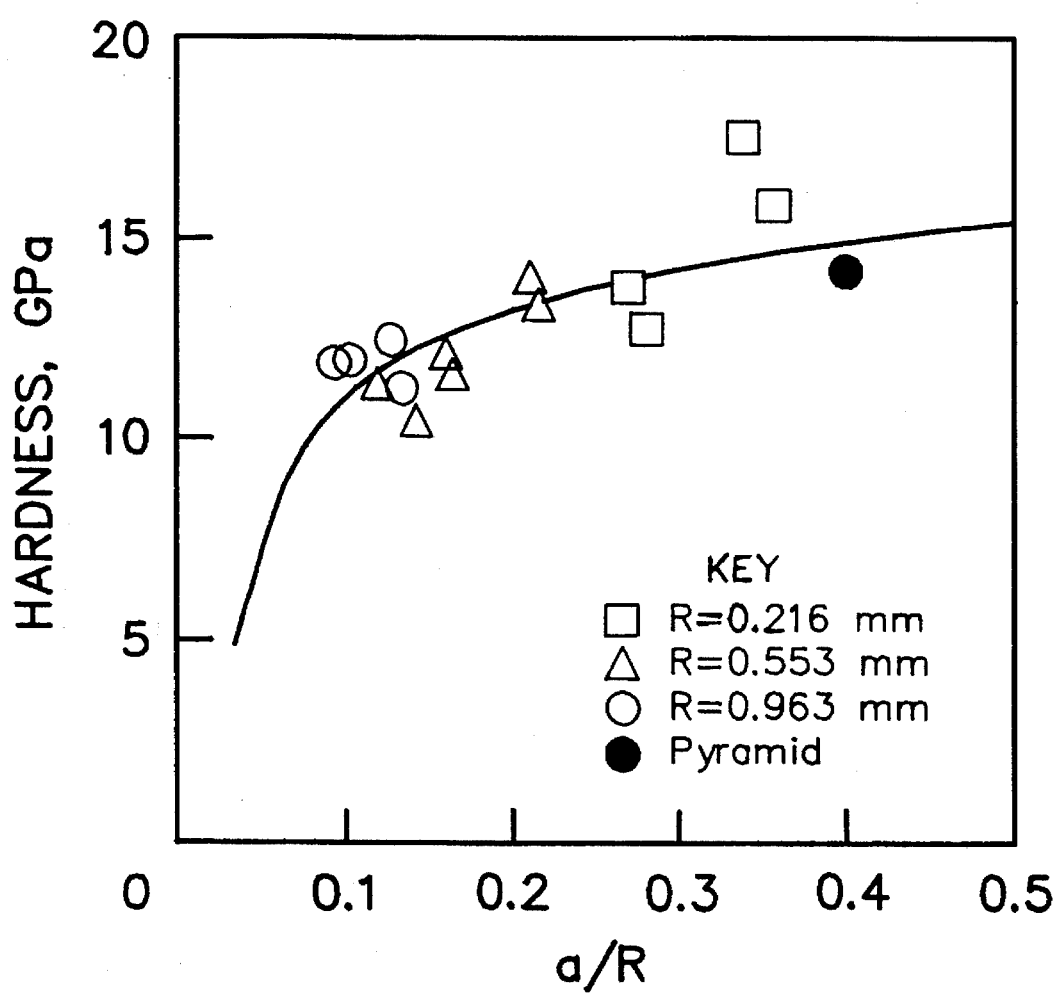
FIG. 8 shows hardness variation as a function of the ratio a/R for alumina indented with diamonds. Vickers hardness is plotted at the equivalent a/R ratio.

A profile through the center of a typical indentation made by a diamond indenter in alumina is shown in FIG. 7. This shows the extent of permanent plastic deformation around the indentation. The plastic deformation causes pile-up of material around the indentation. The residual height, $h_p$, for this indentation is 0.0204 mm, the depth, $d_p$, is 0.0184 mm and the ratio, $B_p$, of the height to depth is 1.11. The variation of hardness as defined by equation 1 for alumina indented with diamonds is shown in FIG. 8. There is an increase in the hardness as the ratio a/R increases. A non-linear least squares fitting routine was used to calculate the Meyer's law constants, $K_1$ and $m_1$, for the alumina using equation 48. The term containing $K_2$ and $m_2$ in equation 48 was set to zero, since the diamond indenters did not plastically deform. The elastic constants for the alumina (as supplied by the manufacture) are E=372 GPa and v=0.22. The elastic constant for the diamond, $k_2$, was 2618 GPa based on elastic modulus, E, of 793 GPa and Poisson's ratio, v, of 0.22. A wide range of elastic properties has been noted for diamond, and E-793 GPa is in the middle of this range. The resulting Meyer's law constants for alumina are $K_1$=18.7 GPa and $m_1$=0.12. From equation 11, the yield stress for the alumina is 3.20 GPa (326 kgf/mm$^2$).

Figure 9:
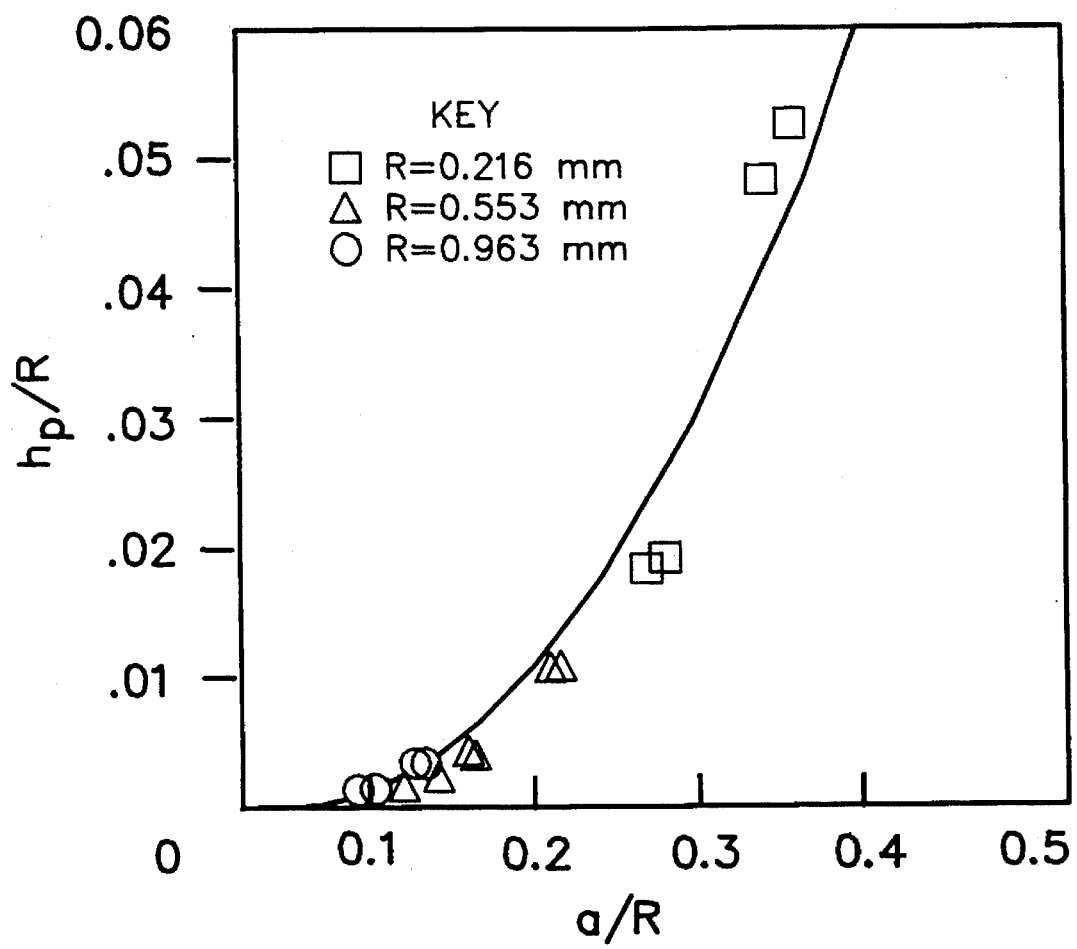
FIG. 9 shows the ratio of residual height to indenter radius, $h_p/R$, as a function of a/R for alumina indented with diamonds.

The residual heights, $h_p$, of the indentations made by diamonds in the alumina is shown in FIG. 9. The residual heights from the plastic portion of equation 45 (equation 50) is also shown in FIG. 9.

$$h_p = a \left[ \frac{u}{K_1} \right]^{\frac{1}{m_1}} \quad (50)$$

The calculated heights are in good agreement to the experimental data, indicating the elastic-plastic model correctly accounts for the displacements of the surface during the indentation. The ratio, $B_p$, of the height to the depth for the indentation in alumina by the diamonds were calculated and averaged. The average value was 1.12±0.08. This is in good agreement with the calculated value of 1.10 for m=1/10. There was a small trend in the $B_p$ values as a function of a/R. The values range from a low of 1.00 for small a/R to a high of 1.26 for large a/R ratios. The analysis predicts that the ratio, $B_p$, should be independent of a/R.

Figure 10:
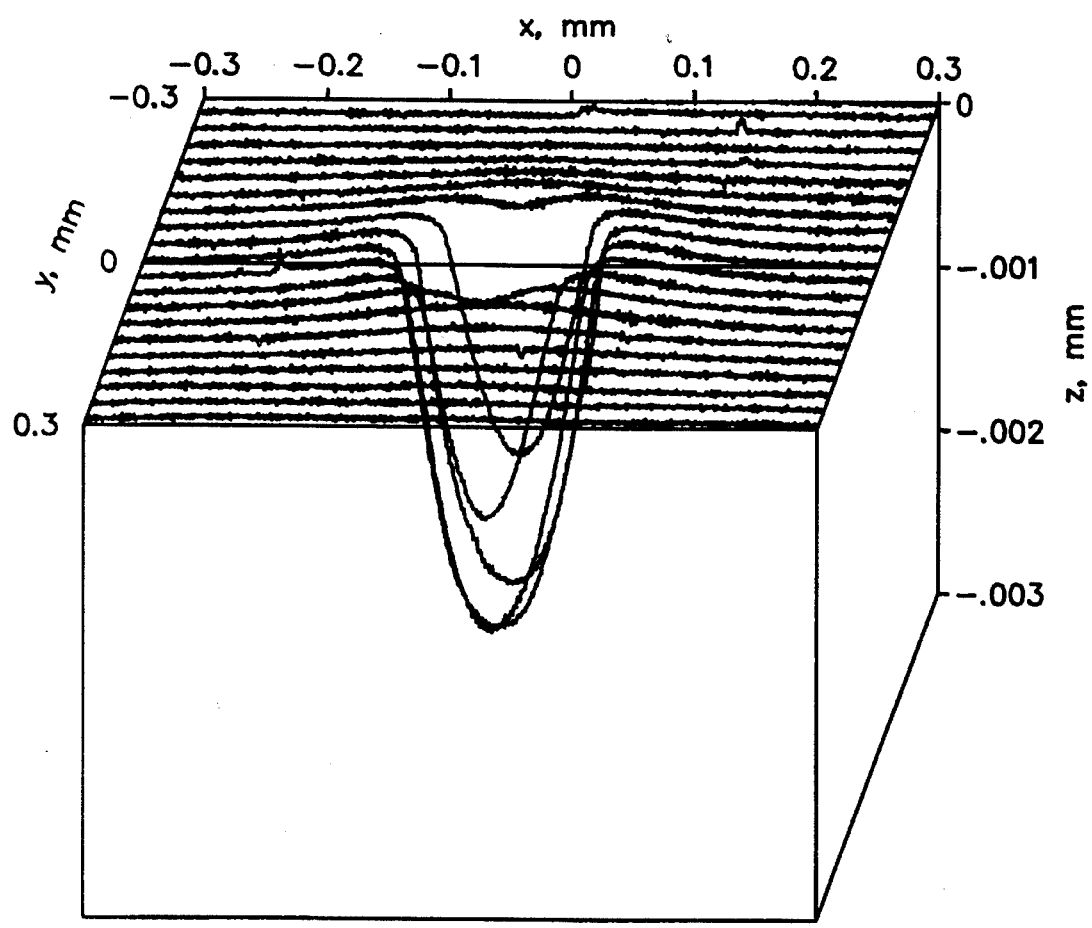
FIG. 10 shows profiles of indentation in WC-Co made by 0.553 mm radius diamond with 302N (30.8 kfg).

Profiles through a typical indentation in the WC-Co are shown in FIG. 10. As with the alumina, there is material piled up around the indentation, but the extent of pile-up is less than for the alumina. The ratio, $B_p$, for this indentation is 1.01.

Figure 11:
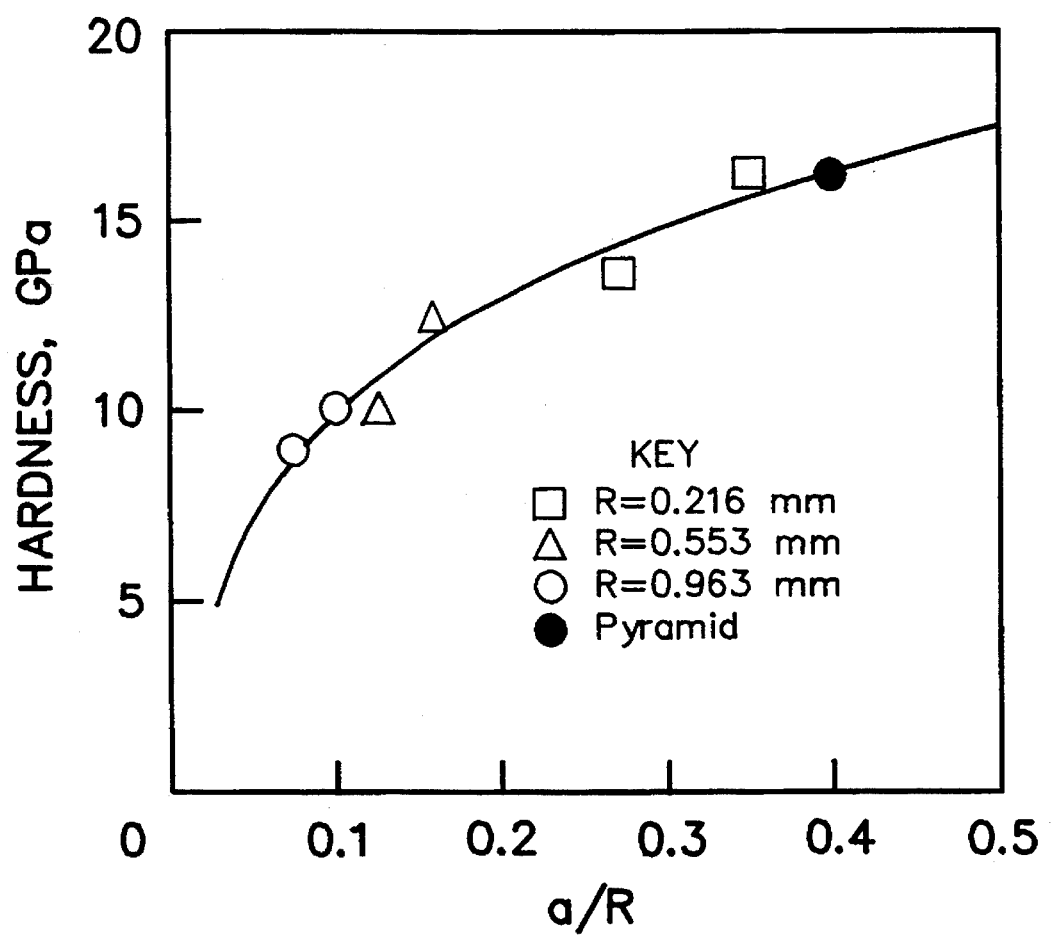
FIG. 11 shows hardness variation as a function of the ratio a/R for WC-Co indented with diamonds. The Vickers hardness is plotted at the equivalent a/R ratio.

The hardness data for the WC-Co is shown in FIG. 11. As with the alumina, the hardness increases with the ratio a/R. The rate of increase of the hardness is greater with the WC-Co than with the alumina. Equation 48 was fit to the data in FIG. 11. The elastic constants for the WC-Co (as supplied by the manufacturer) are E=641GPa and v=0.22. The Meyer's law constants for the WC-Co are $K_1$=26.7 GPa and $m_1$=0.27. The scatter of the data is much less for the WC-Co than with the alumina, since the properties of the WC-Co are much more homogenous and isotropic than the alumina. From equation 11, the yield stress for WC-Co is 1.78 GPa (182 kgf/mm$^2$).

Figure 12:
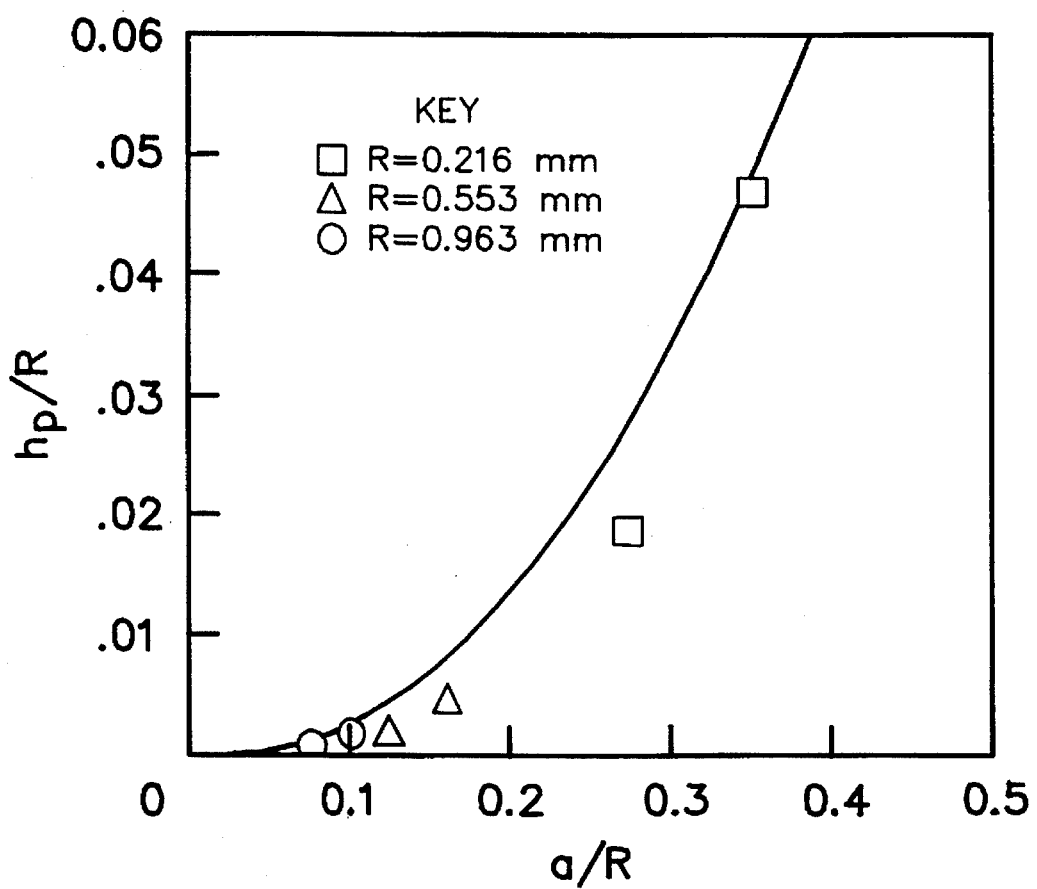
FIG. 12 shows the ratio of residual height to indenter radius, $h_p/R$, as a function of a/R for WC-Co indented with diamonds.

The heights, $h_p$, of the indentation in the WC-Co are shown in FIG. 12. As with the alumina there is good agreement between the data and the analytical model. The ratio, $B_p$, was calculated and averaged for WC-Co indented with diamond. The average value was 1.00±0.05, which is in good agreement with the calculated value of 0.97 for m=¼. As with the alumina, there was a trend in the $B_p$ value as a function of a/R. The values ranged from 0.96 for small a/R to 1.09 for large a/R.

Figure 13:
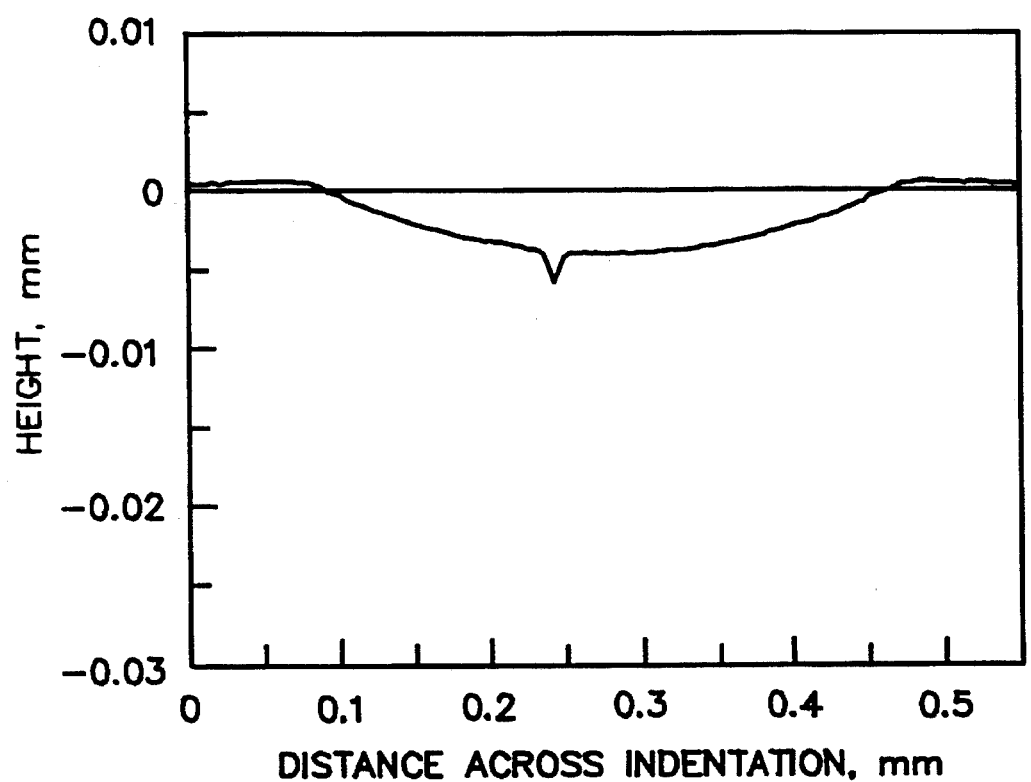
FIG. 13 shows the profile of indentation in alumina made by 1.69 mm radius WC-Co sphere with 1470N (150 kgf).
Figure 14:
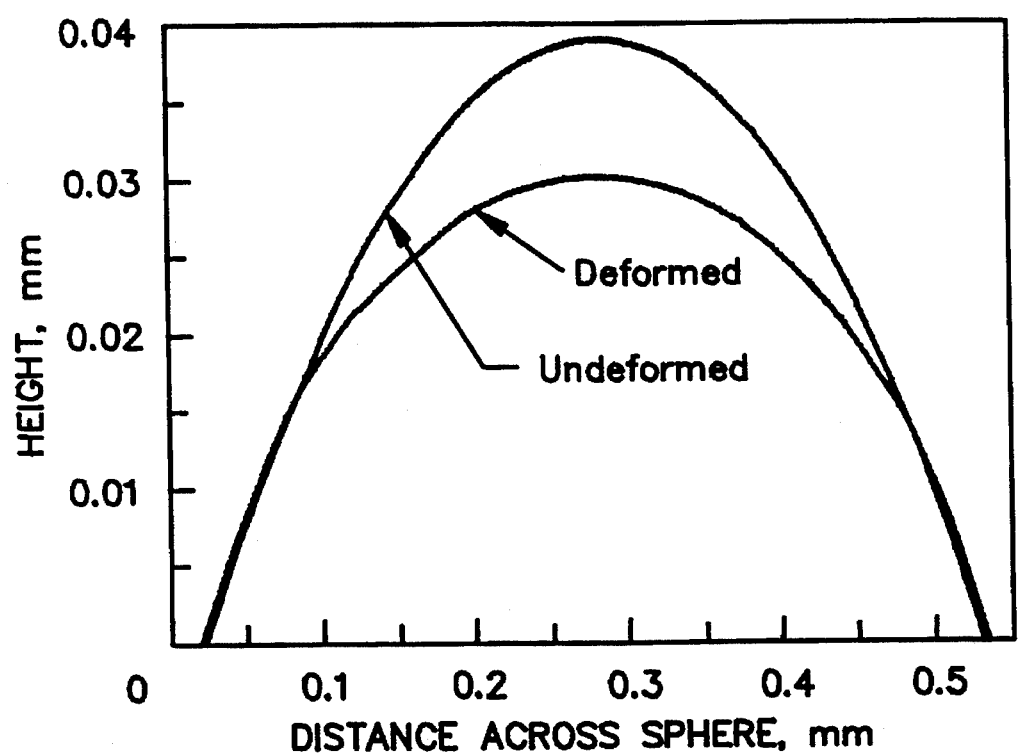
FIG. 14 shows the profile of undeformed and deformed WC-Co sphere used to indent alumina in FIG. 13 with 1470N (150 kgf).
Figure 15:
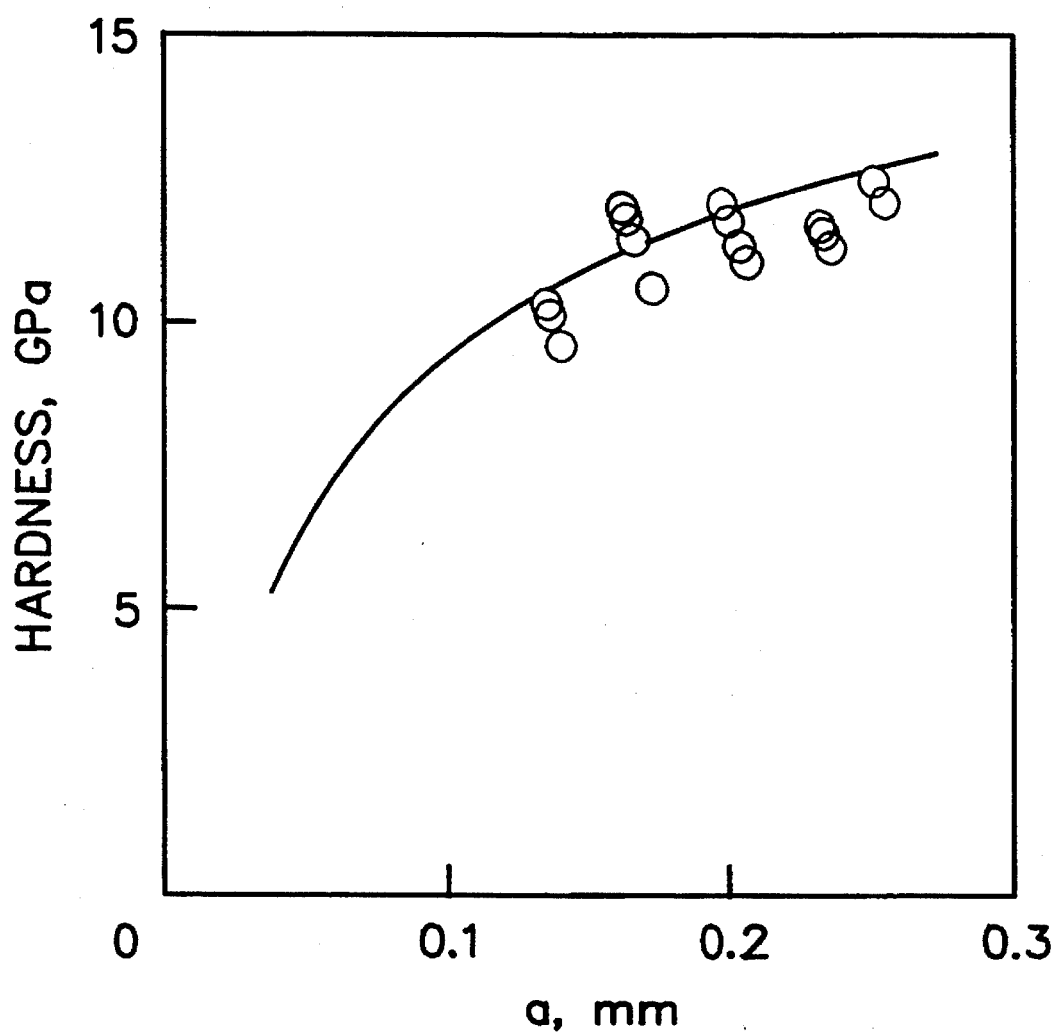
FIG. 15 shows the hardness variation as a function of the contact radius for alumina indented with WC-Co.
Figure 16:
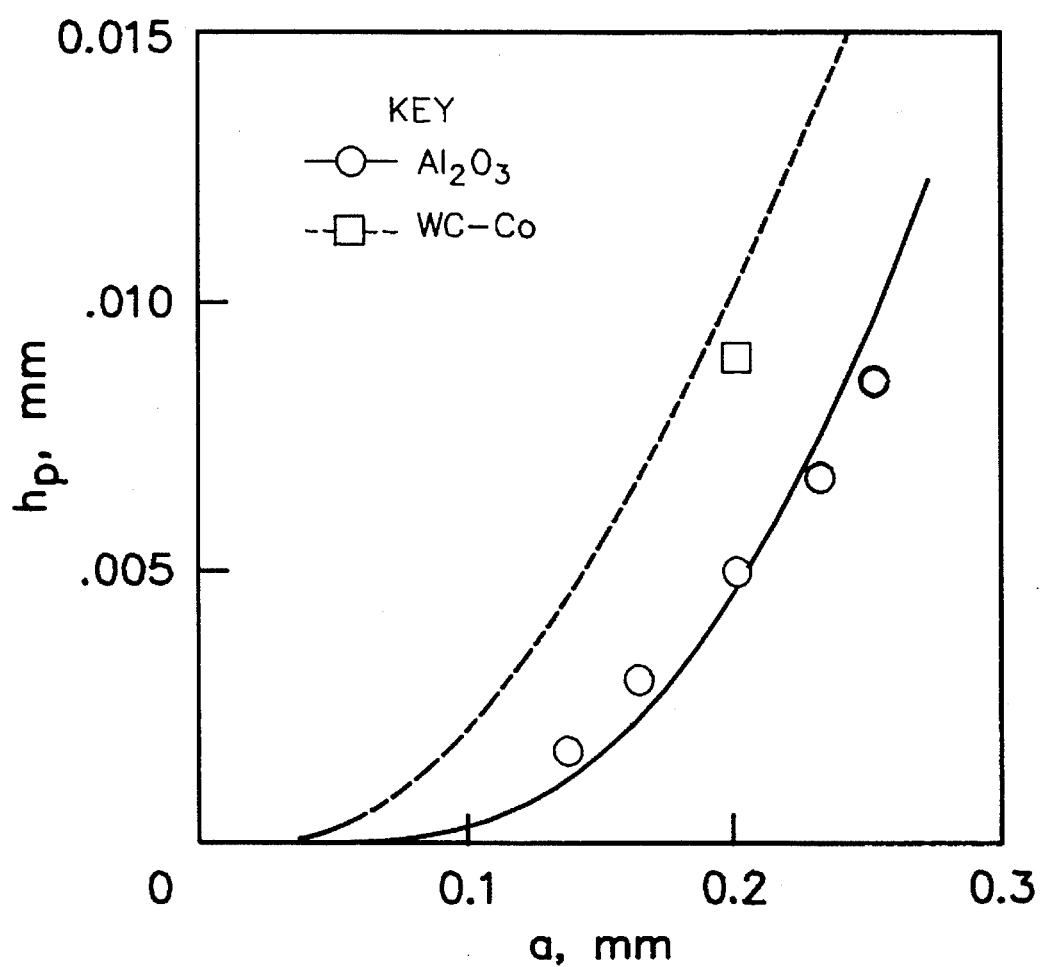
FIG. 16 shows residual height, $h_p$, as a function of contact radius, a, for alumina indented with WC-Co. The height for the flattening of the WC-Co sphere is also shown.

Profiles of a deformed WC-Co ball and the alumina indented by the ball are shown in FIGS. 13 and 14. These two Figures are plotted to the same scale to show the relative contributions to the height, h. The residual deformed heights, $h_{p2}$, for the WC-Co is greater than the residual deformed height, $h_{p1}$, for the alumina. As with the indentations made by the diamond, there is material piled up around the indentation in the alumina. The ratio, $B_p$, of the height to the depth for this indentation is 1.10. The variation of the hardness for the alumina indented with the WC-Co is shown in FIG. 15. The curve in FIG. 15 was calculated using the Meyer's law constants $K_1$, $m_1$, $K_2$ and $m_2$ from the results of the fit to the data in FIGS. 8 and 11. The heights, $h_{p1}$ and $h_{p2}$ are shown in FIG. 16. The curves in FIG. 16 were also calculated from the results of the fit to the data in FIGS. 8 and 11. There is good agreement between the analytical model and the data.

The Vicker's hardness number can be converted to a value that is based on the projected area by dividing by 0.927. This value was compared to the hardness values from spherical indentation in FIGS. 8 and 11. The equivalent a/R value for the Vicker's pyramid is 0.4. The agreement is excellent, especially for the WC-Co. One observation was the plastic height, $h_p$, for the WC-Co was greater than the plastic height for the alumina, even though the Vicker's hardness of the WC-Co is greater than the hardness of the alumina. This illustrates the important role that strain hardening plays in the mechanical response of hard, brittle materials. For purposes of the invention the term brittle is defined as having a fracture ductility of 0.1 or less as defined by ASTM E6.

Most of the indents in the alumina produced ring and radial cracks which were easily visible on the specimen surface. All of the indentations in the alumina produced a family of concentric ring cracks, both partial and completes within the crater. In some cases these cracks were also visible outside the perimeter of the crater. At the lowest load (15 kgf) with the 0.553 mm diamond indenter, no radial cracks were observed and only a few ring cracks were observed. The total number of radial and ring cracks increased as the indentation load increased. Radial cracks appeared to emanate from the outer ring cracks or from the edge of the crater. The subsurface geometry of the radial cracks were observed by fracturing thin alumina disks. The radial cracks had a "quarter penny" geometry and were not coplanar, but intersected along a line below the indentation.

At the highest load (45 kgf) with the 0.216 mm diamond lateral cracking was observed in the alumina specimen. This indentation had an a/R ratio of 0.38. The lateral cracks distorted the residual indentation so that an accurate measurement of the radius, a, and height, $h_p$, could not be made. Lateral cracks were also observed around a Vicker's indentation made with 15 kgf. The Vicker's indentation corresponds to an a/R ratio of 0.4. This indicates the threshold for formation of lateral cracks in this alumina occurs at an a/R ratio between 0.35 and 0.4 for this load range and indenter material.

No cracks were observed in any of the indentations in the WC-Co sample used for FIGS. 11 and 12. All of these indentations were made at loads from 15 to 30 kgf. At a load greater than 30 kgf with the 0.553 mm diamond indenter, the WC-Co ball split into two pieces and could not be used for hardness and height measurements. This indicates the initiation of cracks in the WC-Co occurs at a/R ratios greater than 0.4.

The elastic-plastic analysis provides a means to estimate the yield stress of hard brittle materials. The yield stress of the alumina as calculated from the indentations can be compared to the yield stress measured by other means. The critical resolved shear stress at yield in single crystal alumina at room temperature has been measured to be about 3 GPa under a hydrostatic confining pressure of 1.5 GPa. However this yield occurred by microcracking and not by plastic flow. In a biaxial compression test of polycrystalline alumina the failure occurred at about 0.52 GPa. Considering the differences in test methods and materials, the field stress determined from the indentation tests is in reasonable agreement with these other measurements.

Figure 17:
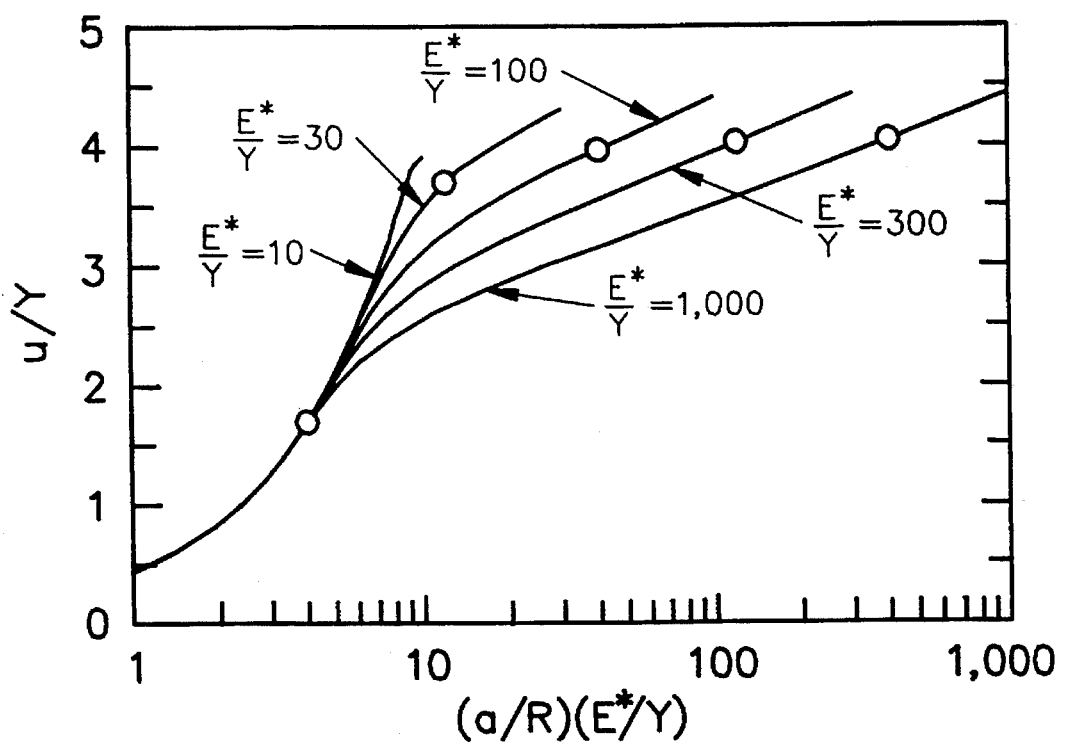
FIG. 17 shows the ratio of mean pressure to yield strength, u/Y, as a function of the dimensionless parameter, (a/R)(E*/Y), for strain hardening of m=0.1, with a variation of elastic modulus to yield strengths. The equivalent values for Vickers indentations are shown with a circle.
Figure 18:
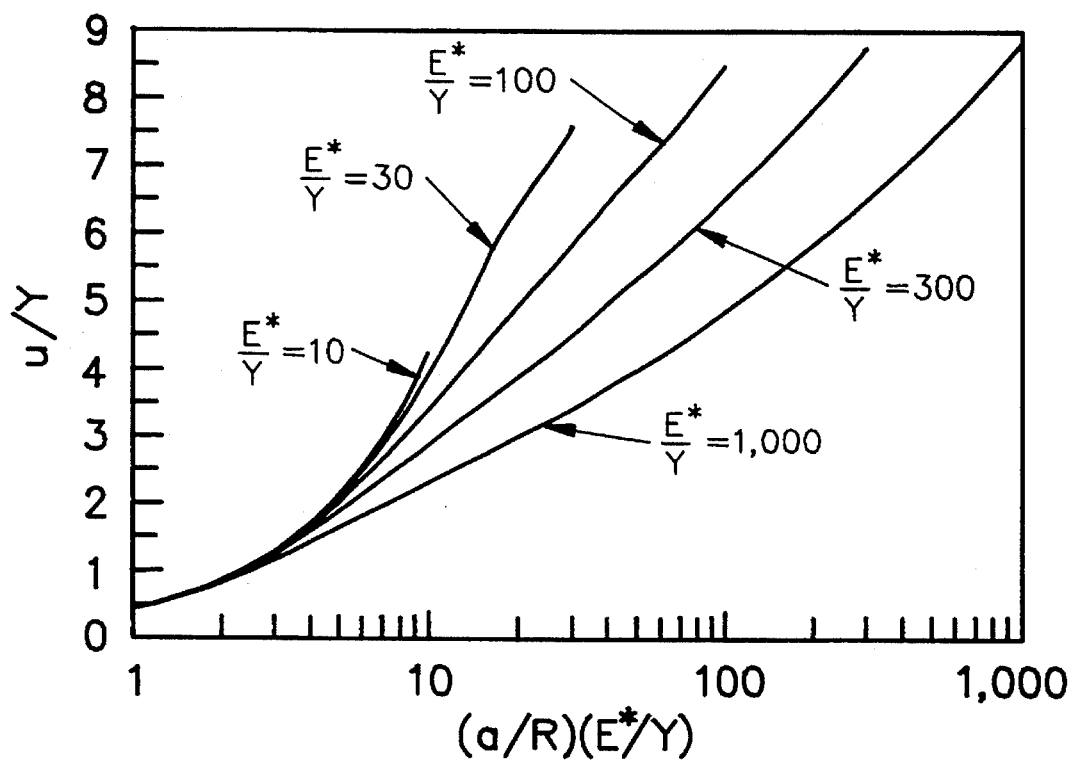
FIG. 18 shows the ratio of mean pressure to yield strength, u/Y, as a function of the dimensionless parameter, (a/R)(E*/Y), for strain hardening of m=0.25, with a variation of elastic modulus to yield strengths.
Figure 19:
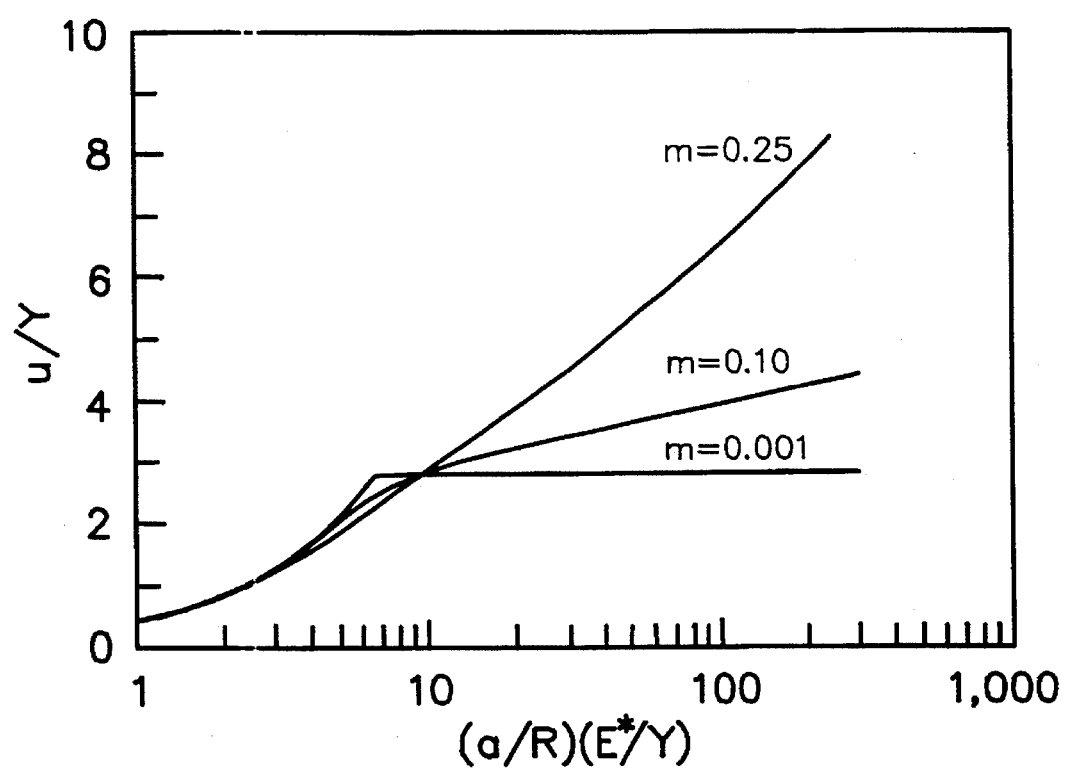
FIG. 19 shows the ratio of mean pressure to yield strength, u/Y, as a function of the dimensionless parameter, (a/R)(E*/Y), with a variation of strain hardening exponent for E*/Y=300.

Others have shown the effects of variation in the elastic modulus to yield strength, E/Y on the mean pressure, u, by plotting the ratio of the mean pressure to the yield strength, u/Y, as a function of the dimensionless parameter, (a/R)(E*/Y), where $E^* = E/(1-v^2)$. In order to compare the present analysis to these other models of indentation, trends of u/Y are shown in FIGS. 17 to 19. FIG. 17 shows the trends for a stain hardening exponents m, of 0.1 with variations in E*/Y. FIG. 18 shows the trends for a strain hardening exponent, m, of 0.25 with variations in E*/Y, and FIG. 19 shows the trends for E*/Y=300 with variations in the strain hardening exponent. Also shown in FIG. 17 is the mean pressure, u/Y, for an a/R ratio of 0.4 which is equivalent to a Vicker's indentation. It can be seen in FIGS. 17 and 18 that a different curve exists for each E*/Y ratio. This is in contrast to earlier analyses which provide one curve to represent the variation of the mean pressure with load for all materials, regardless of the strain hardening exponent. Strain hardening was taken into account in these other analyses by substituting the flow stress for the yield stress. These earlier analyses, while acknowledging that stain hardening influenced the flow stress and hardness, did not address the role of strain hardening on the indentation process.

The analysis describes the displacement of the surface of a hard brittle material by spherical particles. The elastic deflection of an elastic-plastic material by a rigid sphere of radius R is approximately the same as the elastic deflection caused by a rigid sphere of radius $R_e$, where $R_e = a^2/2h_e$ and $h_e$ is calculated by equation 38. These deflections depend only on the pressure distribution, equation 8. At low loads the plastic deformation is insignificant, Re=R, s=1, and $C_1 = \pi^2/8$. As the load increases, plastic deformation occurs, s and $C_1$ change to the values in Table I corresponding no the strain hardening exponent, m, $h_e$ decreases relative to $a^2$ and $R_e$ continuously increases. The plastic deflection of an elastic-plastic material indented by a rigid sphere of radius R is the same as the deflection of a rigid-plastic material indented by a rigid sphere of radius $R_p$. $R_p$ is calculated by equation 18. At low loads, the plastic deformation is insignificant and $R_p$ is infinite. As the load increases, plastic deformation increases and $R_p$ decreases. The minimum value of $R_p$ is R, the radius of the rigid sphere, for situations where the elastic deformation is insignificant.

The load-displacement relationship (equations 44 and 46) provides a basis for better understanding of erosion and abrasion of hard, brittle materials. This relationship may be used to model erosion and abrasion in a way that adds the effects of strain hardening to previous models of erosion and abrasion.

EXAMPLE 2

The variation of hardness as defined by equation 1 for nickel aluminide (NiAl) indented with 1.69 mm diameter WC-Co was measured. There is an increase in the hardness as the ratio a/R increases. A non-linear least squares fitting routine was used to calculate the Meyer's law constants $K_1$ and $m_1$ for the NiAl using equation 48. The elastic constants for the NiAl are E=37 GPa and v=0.31. The elastic constant for the WC-Co, $k_2$ was 2118 GPa based on elastic modulus, E, of 641 GPa and Poisson's ratio, v, of 0.22. The Meyer's law constants for WC-Co are $K_2$= 26.7 GPa and $m_2$=0.27. The resulting Meyer's law constants for NiAl are $K_1$=5.90 GPa and $m_1$=0.31. From equation 11, the yield stress for the NiAl is 209 MPa (21.3 kgf/mm$^2$).

EXAMPLE 3

The variation of hardness as defined by equation 1 for magnesium oxide (MgO) indented with 1.69 diameter WC-Co was measured. There is an increase in the hardness as the ratio a/R increases. A non-linear least squares fitting routine was used to calculate the Meyer's law constants $K_1$ and $m_1$ for the MgO used in equation 48. The elastic constants for the NiAl are E=276 GPa and v=0.20. The elastic constant for the WC-Co, $k_2$ was 2118 GPA based on elastic modulus, E, of 641 GPa and Poisson's ratio v, of 0.22. The Meyer's law constants for WC-Co are $K_2$=26.7 GPa and $m_2$=0.27. The resulting Meyer's law constants for MgO are $K_1$=5.28 GPa and $m_1$=0.13. From equation 11, the yield stress for the MgO is 945 MPa (96.4 kgf/mm$^2$).

TABLE I

Strain Hardening Exponent, m, Profile Shape Ratio, B or $B_p$, Pressure Distribution Exponent, s, and Elastic Deflection Constants $C_1$ and $C_2$

| m | B or $B_p$ | s | $C_1$ | $C_2$ |
|---|---|---|---|---|
| 1 | ½ | 1 | 3.7011 | 7.4022 |
|   |   |   | ($3\pi^2/8$) | ($3\pi^2/4$) |
| ½ | 0.80 | 0.76 | 3.140 | 7.187 |
| ¼ | 0.97 | 0.66 | 2.943 | 7.076 |
| 1/10 | 1.10 | 0.64 | 2.909 | 7.055 |
|   |   | 0 | 2.283 | 6.283 |
|   |   |   | ($2\pi-4$) | ($2\pi$) |

The analysis of the contact mechanics between spherical indenters and elastic-plastic materials takes in account the combined effects of strain hardening and elastic deformation. The results include the contact pressure distribution, the elastic displacements of the surface and the plastic displacements of the surface. Both the residual displacement of the surface and the displacement under loaded conditions result. Measurements on alumina and tungsten carbide-cobalt indicate that there is good agreement between predicted and measured displacements of the surface of these materials.

What is claimed is:

1. A process for measuring the plastic and elastic deformation of a hard, brittle material having a strain to failure in a tensile test of about 0.1 or less which comprises:

(a) indenting a hard, brittle material with a rigid, solid, spherical indenter having a sphere radius of at least about 2 micrometers and a hardness of at least about 1/2.5 times the hardness of the brittle material; and (b) measuring at least one of the contact diameter plastic deformation and contact depth plastic deformation resulting from the indenting; and (c) calculating $K_2$ and $m_2$ for the spherical indenter; and (d) calculating $K_1$ and $m_1$ for the brittle material according to at least one of the equations:

$$a = \left[ \frac{C_1 u}{K_1} + \frac{C_1 u}{K_2} + \left[ \frac{u}{K_1} \right]^{\frac{1}{m_1}} + \left[ \frac{u}{K_2} \right]^{\frac{1}{m_2}} \right] D$$

$$d = \frac{C_2 u a}{K_1} + \frac{C_2 u a}{K_2} + \frac{a}{B_p}\left[ \frac{u}{K_1} \right]^{\frac{1}{m_1}} + \frac{a}{B_p}\left[ \frac{u}{K_2} \right]^{\frac{1}{m_2}}$$

wherein $$u = \frac{L}{\pi a^2}$$

$$K_1 = \frac{\pi E_1}{(1 - v_1^2)}$$

$$K_2 = \frac{\pi E_2}{(1 - v_2^2)}$$

$B_p = 1.18028 - 0.85730 \, m_1 + 0.17761 \, m_1^2$ $C_1 = 2.87339 + 0.19495 \, m_1 + 0.63433 \, m_1^2$ $C_2 = 7.02098 + 0.24729 \, m_1 + 0.13521 \, m_1^2$ a is the contact radius of the brittle material, $C_1$, and $C_2$ are deflection constants, $B_p$ is the profile shape ratio; $k_1$ is the elastic constant for the brittle material, $k_2$ is the elastic constant for the spherical indenter, u is the mean pressure applied; $K_1$ is the Meyer's law constant for the brittle material, $K_2$ is the Meyer's law constant for the spherical indenter, $m_1$ is the strain hardening exponent for the brittle material, $m_2$ is the strain hardening exponent for the spherical indenter, D is the diameter of the spherical indenter; d is the contact depth; L is the applied load, $E_1$ is the elastic modulus for the brittle material, $E_2$ is the elastic modulus for the spherical indenter, and $v_1$ is the Poisson's ratio for the brittle material and $v_2$ is the Poisson's ratio for the spherical indenter.

2. The process of claim 1 wherein the spherical indenter has a hardness greater than that of the sample.

3. The process of claim 1 wherein the spherical indenter is comprised of a material selected from the group consisting of steel, diamond and tungsten-carbide-cobalt.

4. The process of claim 1 wherein steps (a) and (b) are conducted with a brittle material and a sphere such that the ratio a/D is $\geq 0.01$ wherein a is the radius of the contact area indented by the spherical indenter and D is the diameter of the sphere.

5. The process of claim 1 wherein the spherical indenter indents the brittle material with a force of at least 25 micronewtons.

6. The process of claim 1 wherein the spherical indenter indents the brittle material with a force ranging from about 9.8 millinewtons to about 29,400 newtons.

7. The process of claim 1 wherein the spherical indenter having a sphere radius ranging from about 2 micrometers to about 5 millimeters.

8. The process of claim 1 wherein the spherical indenter is a spherically tipped cone having a cone angle ranging from about 90° to about 150°.

9. The process of claim 1 wherein the spherical indenter has a hardness greater than about 2.5 times the hardness of the brittle material.

10. The process of claim 1 wherein the brittle material has a strain to failure ratio of less than about 0.01.

11. The process of claim 1 wherein brittle material is polished prior to indenting.

12. The process of claim 1 wherein the brittle material is polished prior to indenting to a finish of less than about 1 micrometer.

13. The process of claim 1 wherein the brittle material is a ceramic material.

14. The process of claim 1 wherein the brittle material is comprises a metal, intermetallic or rock.

15. A method of fracturing a brittle material and determining the elastic and plastic deformation thereof which comprises (A) providing a hard, brittle material having a strain to failure in a tensile test of about 0.1 or less;

(B) providing a rigid, solid, spherical indenter having a sphere radius of at least about 2 micrometers and a hardness of at least about 1/2.5 times the hardness of the brittle material; and (C) deforming the hard, brittle material by indenting it with the spherical indenter;

(D) measuring at least one of the contact diameter plastic deformation and contact depth plastic deformation resulting from the indenting; and (E) calculating $K_2$ and $m_2$ for the spherical indenter; and (F) calculating $K_1$ and $m_1$ for the brittle material according to at least one of the equations:

$$a = \left[ \frac{C_1 u}{K_1} + \frac{C_1 u}{K_2} + \left[ \frac{u}{K_1} \right]^{\frac{1}{m_1}} + \left[ \frac{u}{K_2} \right]^{\frac{1}{m_2}} \right] D$$

$$d = \frac{C_2 u a}{K_1} + \frac{C_2 u a}{K_2} +$$

$$\frac{a}{B_p} \left[ \frac{u}{K_1} \right]^{\frac{1}{m_1}} + \frac{a}{B_p} \left[ \frac{u}{K_2} \right]^{\frac{1}{m_2}}$$

wherein $$u = \frac{L}{\pi a^2}$$

$$K_1 = \frac{\pi E_1}{(1 - v_1^2)}$$

$$K_2 = \frac{\pi E_2}{(1 - v_2^2)}$$

$B_p = 1.18028 - 0.85730\ m_1 + 0.17761\ m_1^2$ $C_1 = 2.87339 + 0.19495\ m_1 + 0.63433\ m_1^2$ $C_2 = 7.02098 + 0.24729\ m_1 + 0.13521\ m_1^2$ a is the contact radius of the brittle material, $C_1$, and $C_2$ are deflection constants, $B_p$ is the profile shape ratio; $k_1$ is the elastic constant for the brittle material, $k_2$ is the elastic constant for the spherical indenter, u is the mean pressure applied; $K_1$ is the Meyer's law constant for the brittle material, $K_2$ is the Meyer's law constant for the spherical indenter, $m_1$ is the strain hardening exponent for the brittle material, $m_2$ is the strain hardening exponent for the spherical indenter, D is the diameter of the spherical indenter; d is the contact depth; L is the applied load, $E_1$ is the elastic modulus for the brittle material, $E_2$ is the elastic modulus for the spherical indenter, and $v_1$ is the Poisson's ratio for the brittle material and $v_2$ is the Poisson's ratio for the spherical indenter.

16. The method of claim 15 wherein the hard, brittle material is a material which fractures prior to plastically deforming when tensile loads are applied.

17. The method of claim 15 wherein the hard, brittle material is selected from the group consisting of ceramics, metals, intermetallics and rock.

18. The process of claim 15 wherein the spherical indenter is comprised of a material selected from the group consisting of steel, diamond and tungsten-carbide-cobalt.

19. The process of claim 15 wherein the spherical indenter indents the brittle material with a force of at least 25 micronewtons.

20. The process of claim 15 wherein the spherical indenter is a spherically tipped cone having a cone angle ranging from about 90° to about 150° and a sphere radius ranging from about 2 micrometers to about 5 millimeters.

* * * * *